United States Patent
Wagner et al.

(10) Patent No.: US 6,613,931 B1
(45) Date of Patent: Sep. 2, 2003

(54) USE OF PHENYLACETAMIDES AS PLANT PROTECTIVES HAVING HERBICIDAL AND FUNGICIDAL EFFECT

(75) Inventors: Oliver Wagner, Neustadt (DE); Thomas Grote, Schifferstadt (DE); Eberhard Ammermann, Heppenheim (DE); Siegfried Strathmann, Limburgerhof (DE); Gisela Lorenz, Neustadt (DE); Klaus Grossmann, Neuhofen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/913,978

(22) PCT Filed: Feb. 21, 2000

(86) PCT No.: PCT/EP00/01409

§ 371 (c)(1),
(2), (4) Date: Aug. 21, 2001

(87) PCT Pub. No.: WO00/51431

PCT Pub. Date: Sep. 8, 2000

(30) Foreign Application Priority Data

Mar. 2, 1999 (DE) ......................... 199 09 037

(51) Int. Cl.$^7$ ........................................... C07C 255/03
(52) U.S. Cl. ...................................................... 558/392
(58) Field of Search ................. 558/388, 390, 558/392

(56) References Cited

U.S. PATENT DOCUMENTS 4,710,514 A * 12/1987 Takahashi et al. .......... 514/485
4,740,228 A   4/1988 Kis-Tamás et al. ............ 71/77
5,190,999 A   3/1993 Mesvadba .................... 524/96

FOREIGN PATENT DOCUMENTS

GB   1305485      1/1973
WO   WO 95/35283  12/1995

OTHER PUBLICATIONS

White, A.D. et al (1996): J. Med. Chem. 39, 3908–3919.*
Knabe et al. "Acylanilides. I. Syntheses of the Racemates and Enantiomers of Chirla Acylanilides" Arch. Pharm. vol. 321 No. 2 (1988) pp. 107–110.
Knabe et al. "Acylanilides III. Formation of Methemoglobin and its metabolism in rats" Arch Pharm. vol. 321, No. 10 (1988) pp. 739–741.
Bourdais et al. "Une Syntheses Directe Des Indole–Carboxamides–3: Nouvel Acces Aus Derives de La Gramine" Tetrahedron Letters No. 3 (1970) pp. 195–198.
Germain et al. "Synthèses d'indoles par cyclisation réductrice. II. (I) Nouvelle méthode des synthèse des indole carboxamides–3,donnant accés aus dérivés de la gramine" J. Heterocyclic Chem. vol. 13, (1976) pp. 1209–1218.
Hessler "On Phenylmalonic Nitrile" J. Am. Chem. vol. 39 (1908) pp.63–80.
Andrea et al. "Electrophile Aminierung von C–H–aciden Verbindungen mit 1–Oxa–2–azaspiro[2.5]octan" Liebigs Ann. Chem. (1992) pp. 239–256.
White et al. "Heterocyclic Amides: Inhibitors of Acyl–CoA: Cholesterol O–Acyl Transferase with Hypocholesterolemic Activity in Serveral Species and Antiatherosclerotic Activity in the Rabbit" J. Med. Chem. vol. 39 (1996) 3908–3919.

* cited by examiner

Primary Examiner—Joseph K. McKane
Assistant Examiner—Golam M M Shameem
(74) Attorney, Agent, or Firm—Keil & Weinkauf

(57) ABSTRACT

The resent invention relates to the use of phenylacetamides as crop protection agents, to novel crop protection compositions comprising, as active compounds, phenylacetamides, and to novel phenylacetamides.

The present invention provides the use of phenylacetamides of the formula I

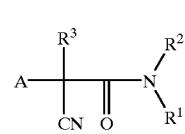

as crop protection agents having herbicidal and/or fungicidal action, where the radicals have the following meanings:

A is an unsubstituted or substituted aryl radical;

$R^1$ is an unsubstituted or substituted aryl radical;

$R^2$, $R^3$ are hydrogen, $C_1$–$C_6$-alkyl, $C_2$–$C_6$-alkenyl, $C_3$–$C_7$-cycloalkyl, $C_1$–$C_6$-alkylaryl, which may be unsubstituted or partially or fully halogenated or may carry one to three substituents selected from the group consisting of $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl;

$R^4$ is hydrogen or $C_1$–$C_6$-alkyl;

$R^5$ is hydroxyl, $C_1$–$C_4$-alkoxy, aryl-$C_1$–$C_4$-alkoxy, aryloxy, and their agriculturally useful salts.

25 Claims, No Drawings

USE OF PHENYLACETAMIDES AS PLANT PROTECTIVES HAVING HERBICIDAL AND FUNGICIDAL EFFECT

This application is a 371 of PCT/EP00/01409 filed Feb. 21, 1999.

The present invention relates to the use of phenylacetamides as crop protection agents, to novel crop protection compositions comprising, as active compounds, phenylacetamides, and to novel phenylacetamides.

The present invention provides the use of phenylacetamides of the formula I

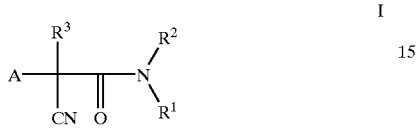

as crop protection agents, where the radicals have the following meanings:

A is aryl which can be mono- or polysubstituted by the following groups: hydrogen, halogen, cyano, nitro, hydroxyl, mercapto, thiocyanato, carboxyl, amino, $C_1$–$C_6$-alkyl, $C_1$–$C_6$-alkoxy-$C_1$–$C_6$-alkyl, $C_1$–$C_6$-cyanoalkyl, $C_2$–$C_6$-alkyenyl, $C_1$–$C_6$-alkoxy-$C_2$–$C_6$-alkenyl, $C_2$–$C_6$-alkynyl, $C_1$–$C_6$-alkoxy-$C_3$–$C_6$-alkynyl, $C_3$–$C_6$-alkynyl–$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkoxy, $C_1$–$C_6$-alkyl-$C_3$–$C_7$-cycloalkoxy, $C_3$–$C_7$-halocycloalkyl, $C_3$–$C_7$-cyanocycloalkyl, $C_3$–$C_7$-halocycloalkoxy, $C_5$–$C_7$-cycloalkenyl, $C_1$–$C_6$-alkyl-$C_5$–$C_7$-cycloalkenyl, $C_1$–$C_6$-alkoxy-$_5$–$C_7$-cycloalkenyl, $C_5$–$C_7$-cyanocycloalkenyl, $C_5$–$C_7$-halocycloalkenyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxyl-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulfinyl, arylsulfonyl, heteroarylsulfinyl, heteroarylsulfonyl, aryl-$C_1$–$C_6$-alkyl, aryl-$C_2$–$C_6$-alkenyl, aryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, $C_1$–$C_6$-alkylsulfinyl, $C_1$–$C_6$-alkylsulfonyl, $C_1$–$C_6$-alkylamino, di-$C_1$–$C_6$-alkylamino, aryl, aryloxy, arylthio or —$C(R^4)$=$NR^5$, $R^1$ is aryl or aryl-$C_1$–$C_6$-alkyl, where the aryl radical can in each case be mono- or polysubstituted by the following groups: hydrogen, halogen, cyano, nitro, hydroxyl, mercapto, thiocyanato, carboxyl, amino, $C_1$–$C_6$-alkyl, $C_1$–$C_6$-alkoxy- $C_1$–$C_6$-alkyl, $C_1$–$C_6$-cyanoalkyl, $C_2$–$C_6$-alkenyl, $C_1$–$C_6$-alkoxy- $C_2$–$C_6$-alkenyl, $C_2$–$C_6$-alkynyl, $C_1C_6$-alkoxy- $C_3$–$C_6$-alkynyl, $C_3$–$C_6$-alkynyl-$C_1C_6$-alkoxy, $C_3$–$C_7$-cycloalkyl, $C_1$–$C_6$-alkyl-$C_3$–$C_7$-cycloalkyl, $C_1$–$C_6$-alkoxy- $C_3$–$C_7$-cycloalkyl, $C_3$–$C_7$-cycloalkyloxy, $C_3$–$C_7$-cyanocycloalkoxy, $C_1$–$C_6$-alkyl-$C_3$–$C_7$-cycloalkoxy, $C_3$–$C_7$-halocycloalkyl, $C_3$–$C_7$-cyanocycloalkyl, $C_3$–$C_7$-halocycloalkoxy, $C_5$–$C_7$-cycloalkenyl, $C_1$–$C_6$-alkyl- $C_5$–$C_7$-cycloalkenyl, $C_1$–$C_6$-alkoxy- $C_5$–$C_7$-cycloalkenyl, $C_5$–$C_7$-cyanocycloalkenyl, $C_5$–$C_7$-halocycloalkenyl, $C_1$–$C_6$-haloalkyl, $C_{2C6}$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_{-C6}$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxyl- $C_1$–$C_6$-alkyl, $C_1$–$C_6$-alkylcarbonyl- $C_1$–$C_6$-alkyl, $C_1$–$C_6$-alkylcarbonylamino, arylcarbonylamino, arylsulfinyl, arylsulfonyl, heteroarylsulfinyl, heteroarylsulfonyl, aryl-$C_1$–$C_6$-alkyl, aryl-$C_2$–$C_6$-alkenyl, aryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, $C_1$–$C_6$-alkylsulfinyl, $C_1$–$C_6$-alkylsulfonyl, $C_1$–$C_6$-alkylamino, di-$C_1$–$C_6$-alkylamino, aryl, aryloxy, arylthio or —$C(R^4)$=$NR^5$, $R^2$, $R^3$ are hydrogen, $C_1$–$C_6$-alkyl, $C_2$–$C_6$-alkenyl, $C_3$–$C_7$-cycloalkyl, $C_1$–$C_6$-alkylaryl, which may be unsubstituted or partially or fully halogenated or may carry one to three substituents selected from the group consisting of $C_1$–$C_4$-alkoxy, $C_1$–$C_4$-haloalkoxy, $C_1C_4$-alkylthio, $C_3$–$C_7$-cycloalkyl, $C_5$–$C_7$-cycloalkenyl;

$R^4$ is hydrogen or $C_1$–$C_6$-alkyl, $R^5$ is hydroxyl, $C_1$–$C_4$-alkoxy, aryl- $C_1$–$C_4$-alkoxy, aryloxy, and their agriculturally useful salts.

Some of the compounds of the formula I are known from the literature.

WO 95/35283 describes trisubstituted phenyl derivatives as medicaments which act as PDE IV (phosphodiesterase IV) inhibitors. It describes in particular compounds of the following formula

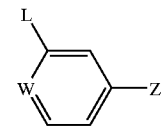

where W is, inter alia, the group =C(Y)—, where Y=halogen, alkyl, —X—$R^a$ or —N($R^b$), where X=O, S, SO, SO₂; $R^a$=hydrogen, alkyl; $R^b$=hydrogen or alkyl; L=—CH($R^1$)($R^2$) where $R^1$ and $R^2$=CN or —CONR⁹R¹⁰ and $R^9$ and $R^{10}$=hydrogen, alkyl, aralkyl or aryl; Z=one of the groups (A)–(D), described in more detail therein, where these groups have to be substituted by at least one aryl group (Ar).

EP 0 466 640 describes alpha-carbonylphenylacetonitrile derivatives as stabilizers for organic materials. The compounds of the formula

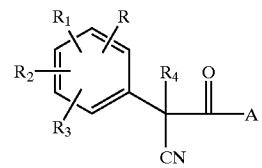

which are disclosed in that publication are suitable for stabilizing lubricating oils, fluids for processing metals, hydraulic fluids and thermoplastic polymers and elastomers. In the formula shown above, A is, inter alia, the group —NR⁶R⁷, where $R^6$, $R^7$ may, inter alia, be hydrogen and unsubstituted phenyl or naphthyl. Two radicals R, $R^1$, $R^2$, $R^3$ or $R^4$ which are attached ortho to one another may also form the group —CH=CH—CH=CH—(naphthyl group).

DD 156,663 describes compounds of the formula below for use as plant growth stimulating agents for use in crop plants, such as, for example, maize, sunflower, tomato, soybean or beans:

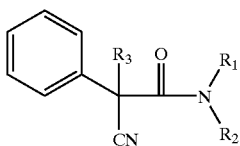

The radicals have, inter alia, the following meanings: $R_1$, $R_2$: hydrogen, alkyl, cycloalkyl, aryl, haloaryl, aralkyl, alkenyl or alkanoyl; $R_3$: hydrogen or alkyl. The compounds described are characterized by the fact that the phenyl group is in each case unsubstituted.

DE 2 008 692 describes cyanophenylacetamide derivatives of the formula below

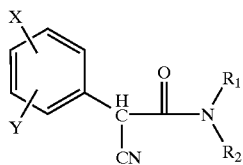

as starting materials or intermediates for preparing indole-3-carboxylic acid derivatives. $R_1$ and $R_2$ are hydrogen, alkyl or aralkyl. The two radicals X and Y on the phenyl ring are, inter alia, hydrogen, halogen, alkyl, alkoxy, aralkoxy, trifluoromethyl, hydroxyl, amino, nitro, carboxyl or sulfoxy. Additionally, the phenyl ring may be substituted by an amino or nitro group.

Furthermore, the following individual compounds of the formula I are known from the scientific literature:

a) The compound where A=phenyl, $R^1$=4-ethoxyphenyl, $R^2$=H, $R^3$=n-$C_4H_9$ [N-(4-ethoxyphenyl)-2-cyano-2-phenylhexanamide] from Arch. Pharm. 321 (1988): 107.

b) The compound where A=phenyl, $R^1$=4-ethoxyphenyl, $R^2$=H, $R^3$=$C_2H_5$; [N-(4-ethoxyphenyl)-2-cyano-2-phenylbutanamide from Arch. Pharm. 321 (1988), 739.

c) The compound where A=phenyl, $R^1$=2,4,6-trimethoxyphenyl, $R^2$=H, $R^3$=H; [N-(2,4,6-trimethoxyphenyl)-2-cyano-2-phenylacetamide] from J. Med. Chem. 39,20 (1996), 3908.

d) The compound where A=4-methoxyphenyl, $R^1$=2,6-dimethylphenyl, $R^2$=H, $R^3$=H; [N-(2,6,-dimethylphenyl)-2-cyano-2-phenylacetamide] from Liebigs Ann. Chem. 3, (1992): 239.

e) The compounds where A=phenyl, $R^1$=2-methylphenyl, 3-methylphenyl or 4-methylphenyl, $R^2$=H, $R^3$=H; [N-(2-methylphenyl)-2-cyano-2-phenylacetamide; N-(3-methylphenyl)-2-cyano-2-phenylacetamide; N-(4-methylphenyl)-2-cyano-2-phenylacetamide] from Am. Chem. J. 39 (1908), 76.

Surprisingly, it has been found that compounds of the formula I can be used as crop protection agents having fungicidal and/or herbicidal action. They are suitable for treating plants, for example for controlling harmful fungi in useful plants (fungicidal action) or for controlling undesirable plant growth in the case of harmful plants (herbicidal action).

Compounds of the formula I can be prepared analogously to the processes known from the literature (for example J. Am. Chem. Soc. 39 (1908), 63; DD 156663). The starting materials are either known from the literature or they can be prepared analogously to methods known from the literature, or they are commercially available.

The present invention furthermore provides crop protection compositions which comprise the compounds of the formula I, with the exception of the compounds described in DD 156,663 as plant-growth-regulating agents. What is meant in this context are in particular crop protection compositions which comprise the compounds I, with the proviso that a) if A is an unsubstituted phenyl group and $R^3$ is hydrogen or alkyl, $R^1$ is not unsubstituted phenyl or halogen-substituted phenyl;

b) if $R^3$ is hydrogen, A is not 2-nitrophenyl or 2-aminophenyl.

The present invention furthermore provides novel compounds of the formula I as described above, except for the compounds described in WO 95/35283, EP 0 466 640, DD 156663 and DE 2008692 and the individual compounds mentioned above under a)–e). What is meant in this context are in particular those compounds of the formula I, with the proviso that a) if A is an unsubstituted phenyl group and $R^3$ is hydrogen or alkyl, $R^1$ is not unsubstituted phenyl or halogen-substituted phenyl;

b) if $R^3$ is hydrogen, A is not 2-nitrophenyl or 2-aminophenyl;

c) if $R^3$ is hydrogen, $R^1$ is hydrogen, alkyl or alkylaryl, A is not phenyl which is substituted directly or indirectly by an aryl group.

In the definition of the different radicals in the formula I, the given terms, either on their own (such as, for example, $C_1$–$C_6$-"alkyl") or as parts of or in combination with other composite chemical groups (such as, for example, $C_1$–$C_6$-halo-"alkyl", alkoxy-$C_1$–$C_6$-"alkyl"), are in principle collective terms for a group of compounds. If the abovementioned groups can be mono- or polysubstituted, the substituents can in principle be identical or different.

Halogen is in each case fluorine, bromine, chlorine or iodine, in particular fluorine or chlorine.

Examples of other meanings are:

$C_1$–$C_4$-alkyl and all alkyl moieties of correspondingly composed chemical groups, such as, for example, alkylamino, dialkylamino, alkylaryl, cyanoalkyl, haloalkyl, etc.: a straight-chain or branched alkyl radical, such as, for example, methyl, ethyl, n-propyl, 1-methylethyl, n-butyl, 1-methylpropyl, 2-methylpropyl or 1,1-dimethylethyl, in particular methyl or ethyl;

$C_1$–$C_6$-alkyl: a straight-chain or branched $C_1$–$C_6$-alkyl radical, such as, for example, $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_2$–$C_6$-alkenyl and all alkenyl moieties of correspondingly composed groups, such as, for example, alkenyloxy, haloalkenyl, haloalkenyloxy, etc.: a straight-chain or branched alkenyl radical, such as, for example, ethylene, prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl and 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimetylbut-2-en-1-yl, 1,2-dimethylbut-3-en-1-yl, 1,3-dimetylbut-1-en-1-yl, 1,3-dimethylbut-2-en-1-yl, 1,3-dimetylbut-3-en-1-yl, 2,2-dimethylbut-3-en-1-yl, 2,3-dimethylbut-1-en-1-yl, 2,3-dimethylbut-2-en-1-yl, 2,3-dimetylbut-3-en-1-yl, 3,3-dimethylbut-2-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-2-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkynyl, and all alkynyl moieties of correspondingly composed chemical groups, such as, for example, alkynyloxy or alkynylalkoxy, etc.: for example ethynyl, propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_1$–$C_6$-haloalkyl is a $C_1$–$C_6$-alkyl radical as mentioned above which is partially or fully substituted by fluorine, chlorine, bromine and/or iodine, for example trichloromethyl, trifluoromethyl, 2-fluoroethyl, 2-chloroethyl, 2-bromoethyl, 2,2-difluoroethyl, 2,2,2-trifluoroethyl, 2,2,2-trichloroethyl, 2-fluoropropyl, 3-fluoropropyl, 2-chloropropyl or 3-chloropropyl, in particular 2-fluoroethyl or 2-chloroethyl;

$C_1$–$C_6$-alkoxy and all alkoxy moieties of correspondingly composed chemical groups, such as, for example, alkoxyalkyl, alkoxyalkenyl, alkoxyalkynyl, alkoxycarbonyl, etc.: a straight-chain or branched alkoxy radical, such as, for example, methoxy, ethoxy, propoxy, 1-methylethoxy, butoxy, 1-methylpropoxy, 2-methylpropoxy and 1,1-dimethylethoxy, in particular methoxy or ethoxy;

halo-$C_1$–$C_6$-alkoxy is a $C_1$–$C_6$-alkoxy radical as mentioned above which is partially or fully substituted by fluorine, chlorine or bromine;

halo-$C_2$–$C_6$-alkenyl is a $C_2$–$C_6$-alkenyl radical as mentioned above which is partially or fully substituted by fluorine, chlorine or bromine;

halo-$C_2$–$C_6$-alkynyl is a $C_2$–$C_6$-alkynyl radical as mentioned above which is partially or fully substituted by fluorine, chlorine or bromine;

$C_3$–$C_8$-cycloalkyl and all cycloalkyl moieties of correspondingly composed chemical groups, such as, for example, cycloalkylalkoxy, alkylcycloalkyl, alkylcycloalkyloxy, cycloalkyloxy, etc.: cyclopropyl, cyclobutyl, cyclopentyl, cyclohexyl, cycloheptyl, cyclooctyl;

$C_3$–$C_8$-cycloalkenyl and all cycloalkenyl moieties of correspondingly composed chemical groups, such as, for example, alkylcycloalkenyl, cyanocycloalkenyl, etc.: cyclopropenyl, cyclobutenyl, cyclopentenyl, cyclohexenyl, cycloheptenyl, cyclooctenyl; $C_1$–$C_6$-alkyl-carbonyl and all alkylcarbonyl moieties of correspondingly composed chemical groups, such as, for example, alkylcarbonylalkyl, alkylcarbonylamino, etc.: a carbonyl group which is substituted by a $C_1$–$C_6$-alkyl radical such as, for example, methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylthio is a sulfur atom which is substituted by a $C_1$–$C_6$-alkyl radical as mentioned above;

$C_1$–$C_6$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl;

aryl and all aryl moieties of correspondingly composed chemical groups, such as, for example, aryl-$C_1$–$C_6$-alkyl, aryl-$C_2$–$C_6$-alkenyl, aryloxy, arylthio, arylcarbonylamino, etc.: a mono-to tricyclic aromatic ring system containing 6–14 carbon ring members, such as, for example, phenyl, naphthyl and anthracenyl;

aryl-$C_1$–$C_6$-alkyl: a straight-chain or branched $C_1$–$C_6$-alkyl group as mentioned above, where the alkyl group is substituted by aryl as mentioned above; such as, for example, arylmethyl, 2-arylethyl, 1-arylethyl, 3-arylpropyl, 2-arylpropyl;

hetaryl and all hetaryl moieties of correspondingly composed chemical groups, such as, for example, hetarylthio, etc.: aromatic mono- or polycyclic five-or six-membered ring systems which, in addition to carbon ring members, may also contain 1 to 4 nitrogen atoms or 1 to 3 nitrogen atoms and one oxygen or one sulfur atom or one oxygen or one sulfur atom;

imino group —C($R^4$)=$NR^5$ is, for example: —HC=NOH, $C_1$–$C_6$-alkyl-C=NOH, —HC=NO-$C_1$–$C_6$-alkyl, —HC=NO-$C_1$–$C_6$-alkylaryl, $C_1$–$C_6$-alkyl-C=NO-$C_1$–$C_6$-alkyl, —HC=NO-$C_2$–$C_6$-alkenyl, $C_1$–$C_6$-alkyl-C=NO-$C_2$–$C_6$-alkenyl, —HC=N-O-aryl or $C_1$–$C_6$-alkyl-C=N-O-aryl.

Depending on the substitution pattern, the compounds of the formula I can contain one or more chiral centers, in which case they are present as enantiomers or mixtures of diastereomers. The invention provides both the pure enantiomers or diastereomers and their mixtures. The ratios can vary, depending on the groups. The mixtures can, if appropriate, be separated by customary methods. The compounds I can be used both as pure isomers and as isomer mixtures.

The compounds of the formula I can also be present in the form of their agriculturally useful salt, the type of salt usually being immaterial. in general, the salts of those cations or the acid addition salts of those acids are suitable whose cations and anions, respectively, do not negatively affect the herbicidal or fungicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, di-(2-hydroxyeth-1-yl) ammonium, (2-(2-hydroxyeth-l-oxy)eth-1-yl]-ammonium, diisopropylammonium, tetramethylammonium, tetrabutylammonium, trimethylbenzylammonium, furthermore phosphonium ions, sulfonium ions, preferably tri($C_1$–$C_4$-alkyl)sulfonium and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and also the anions of $C_1$–$C_4$-alkanoic acids, preferably formate, acetate, propionate and butyrate.

For the purpose of the present invention, preference is given to compounds of the formula I having the following structural features a.–d., where the compounds may have one or more of the structural features a.–d.:

a. A is unsubstituted or substituted phenyl or naphthyl.
b. $R^1$ is unsubstituted or substituted phenyl.
c. $R^2$ is hydrogen.
d. $R^3$ is hydrogen; $C_1$–$C_6$-alkyl, in particular methyl, ethyl, propyl; $C_3$–$C_7$-cycloalkyl, in particular cyclopropyl.

If A or $R^1$ is phenyl, the phenyl ring may be substituted by one to five of the abovementioned radicals, which may be in the 2-, 3- or 4-position. Th e phenyl ring is preferably mono- or disubstituted. Preferred substituents are: halogen, alkyl, alkoxy, nitro, cyano, haloalkyl, phenyl.

In the case of monosubstituted phenyl rings, suitable substituents are in particular the following groups: halogen, such as, for example, fluorine, chlorine; alkyl, such as, for example, methyl; alkoxy, such as, for example, methoxy; nitro; haloalkyl, such as, for example, trifluoromethyl; or cyano. For this purpose, for example the following groups are suitable: 4-halophenyl, 4-alkylphenyl, 4-alkoxyphenyl, 4-nitrophenyl, 4-cyanophenyl, 4-trifluoromethylphenyl, 2-halophenyl, 2-alkylphenyl, 2-alkoxyphenyl, 2-nitrophenyl, 2-cyanophenyl, 2-trifluoromethylphenyl, 3-halophenyl, 3-alkylphenyl, 3-alkoxyphenyl, 3-nitrophenyl, 3-cyanophenyl, 3-trifluoromethylphenyl.

In the case of disubstituted phenyl rings, suitable substituents are in particular the following groups, where the substituents may be identical or different: halogen, such as, for example, chlorine; or alkyl, such as, for example, methyl. For this purpose, for example the following groups are suitable: 2,3-dihalophenyl, 2,4-dihalophenyl, 2,5-dihalophenyl, 2,6-dihalophenyl, 3,4-dihalophenyl, 3,5-dihalophenyl, 2,3-dimethylphenyl, 2,4-dimethylphenyl, 2,5-dimethylphenyl, 2,6-dimethylphenyl, 3,4-dimethylphenyl, or 3,5-dimethylphenyl.

A and $R^1$ are preferably an unsubstituted naphthyl radical or an unsubstituted or substituted phenyl radical, the phenyl radicals being preferably mono- or disubstituted by the abovementioned radicals.

For the purpose of the present invention, for example the following compounds of Table 1 are suitable:

TABLE 1

| | Aryl | $R^3$ | $R^2$ | $R^1$ | m.p. |
|---|---|---|---|---|---|
| 1 | $C_6H_5$ | H | H | 2-Cl—$C_6H_4$ | 114 |
| 2. | $C_6H_5$ | H | H | 3-Cl—$C_6H_4$ | 123 |
| 3. | $C_6H_5$ | H | H | 4-Cl—$C_6H_4$ | 151 |
| 4. | $C_6H_5$ | H | H | 2,3-$Cl_2$—$C_6H_3$ | |
| 5. | $C_6H_5$ | H | H | 2,4-$Cl_2$—$C_6H_3$ | 145 |
| 6. | $C_6H_5$ | H | H | 2,5-$Cl_2$—$C_6H_3$ | |
| 7. | $C_6H_5$ | H | H | 2,6-$Cl_2$—$C_6H_3$ | 184 |
| 8. | $C_6H_5$ | H | H | 3,4-$Cl_2$—$C_6H_3$ | |
| 9. | $C_6H_5$ | H | H | 3,5-$Cl_2$—$C_6H_3$ | 166 |
| 10. | $C_6H_5$ | H | H | 2-$CH_3$—$C_6H_4$ | 138–139 |
| 11. | $C_6H_5$ | H | H | 3-$CH_3$—$C_6H_4$ | 128 |
| 12. | $C_6H_5$ | H | H | 4-$CH_3$—$C_6H_4$ | 134 |
| 13. | $C_6H_5$ | H | H | 2,3-$(CH_3)_2$—$C_6H_3$ | 176 |
| 14. | $C_6H_5$ | H | H | 2,4-$(CH_3)_2$—$C_6H_3$ | 135 |
| 15. | $C_6H_5$ | H | H | 2,5-$(CH_3)_2$—$C_6H_3$ | 164 |
| 16. | $C_6H_5$ | H | H | 2,6-$(CH_3)_2$—$C_6H_3$ | 179 |
| 17. | $C_6H_5$ | H | H | 3,4-$(CH_3)_2$—$C_6H_3$ | |
| 18. | $C_6H_5$ | H | H | 3,5-$(CH_3)_2$—$C_6H_3$ | 136 |
| 19. | $C_6H_5$ | H | H | 4-$CH_3O$—$C_6H_4$ | 127–129 |
| 20. | $C_6H_5$ | H | H | 4-F—$C_6H_4$ | 120–127 |
| 21. | $C_6H_5$ | H | H | 4-CN—$C_6H_4$ | 114–115 |
| 22. | $C_6H_5$ | H | H | 4-$CF_3$—$C_6H_4$ | 149 |
| 23. | $C_6H_5$ | H | H | 4-$NO_2$—$C_6H_4$ | |
| 24. | $C_6H_5$ | H | H | 4-$C_6H_5$—$C_6H_4$ | |
| 25. | $C_6H_5$ | H | H | 2-$CH_3O$—$C_6H_4$ | |
| 26. | $C_6H_5$ | H | H | 2-F—$C_6H_4$ | |
| 27. | $C_6H_5$ | H | H | 2-CN—$C_6H_4$ | |
| 28. | $C_6H_5$ | H | H | 2-$CF_3$—$C_6H_4$ | |
| 29. | $C_6H_5$ | H | H | 2-$NO_2$—$C_6H_4$ | |
| 30. | $C_6H_5$ | H | H | 2-$C_6H_5$—$C_6H_4$ | |

TABLE 1-continued

| | Aryl | R³ | R² | R¹ | m.p. |
|---|---|---|---|---|---|
| 31. | C₆H₅ | H | H | 3-CH₃O—C₆H₄ | |
| 32. | C₆H₅ | H | H | 3-F—C₆H₄ | |
| 33. | C₆H₅ | H | H | 3-CN—C₆H₄ | |
| 34. | C₆H₅ | H | H | 3-CF₃—C₆H₄ | |
| 35. | C₆H₅ | H | H | 3-NO₂—C₆H₄ | |
| 36. | C₆H₅ | H | H | 3-C₆H₅—C₆H₄ | |
| 37. | C₆H₅ | CH₃ | H | 4-CH₃—C₆H₄ | 105–107 |
| 38. | C₆H₅ | CH₃ | H | 4-Cl—C₆H₄ | 129–131 |
| 39. | C₆H₅ | CH₃ | H | 4-CH₃O—C₆H₄ | 117–118 |
| 40. | C₆H₅ | CH₃ | H | 4-F—C₆H₄ | |
| 41. | C₆H₅ | CH₃ | H | 4-CN—C₆H₄ | |
| 42. | C₆H₅ | CH₃ | H | 4-CF₃—C₆H₄ | |
| 43. | C₆H₅ | CH₃ | H | 4-NO₂—C₆H₄ | |
| 44. | C₆H₅ | CH₃ | H | 4-C₆H₅—C₆H₄ | |
| 45. | C₆H₅ | CH₃ | H | 2-CH₃—C₆H₄ | |
| 46. | C₆H₅ | CH₃ | H | 2-Cl—C₆H₄ | |
| 47. | C₆H₅ | CH₃ | H | 2-CH₃O—C₆H₄ | |
| 48. | C₆H₅ | CH₃ | H | 2-F—C₆H₄ | |
| 49. | C₆H₅ | CH₃ | H | 2-CN—C₆H₄ | |
| 50. | C₆H₅ | CH₃ | H | 2-CF₃—C₆H₄ | |
| 51. | C₆H₅ | CH₃ | H | 2-NO₂—C₆H₄ | |
| 52. | C₆H₅ | CH₃ | H | 2-C₆H₅—C₆H₄ | |
| 53. | C₆H₅ | CH₃ | H | 3-CH₃—C₆H₄ | |
| 54. | C₆H₅ | CH₃ | H | 3-Cl—C₆H₄ | |
| 55. | C₆H₅ | CH₃ | H | 3-CH₃O—C₆H₄ | |
| 56. | C₆H₅ | CH₃ | H | 3-F—C₆H₄ | |
| 57. | C₆H₅ | CH₃ | H | 3-CN—C₆H₄ | |
| 58. | C₆H₅ | CH₃ | H | 3-CF₃—C₆H₄ | |
| 59. | C₆H₅ | CH₃ | H | 3-NO₂—C₆H₄ | |
| 60. | C₆H₅ | CH₃ | H | 3-C₆H₅—C₆H₄ | |
| 61. | C₆H₅ | H | H | C₆H₅ | |
| 62. | C₆H₅ | CH₃ | H | C₆H₅ | |
| 63. | C₆H₅ | C₂H₅ | H | 4-Cl—C₆H₄ | |
| 64. | C₆H₅ | C₃H₇ | H | 4-Cl—C₆H₄ | |
| 65. | C₆H₅ | i.C₃H₇ | H | 4-Cl—C₆H₄ | |
| 66. | C₆H₅ | C₄H₉ | H | 4-Cl—C₆H₄ | |
| 67. | C₆H₅ | c-C₃H₅ | H | 4-Cl—C₆H₄ | |
| 68. | 4-Cl—C₆H₄ | H | H | C₆H₅ | |
| 69. | 4-CH₃—C₆H₄ | H | H | C₆H₅ | |
| 70. | 4-OCH₃ | H | H | C₆H₅ | |
| 71. | 4-NO₂—C₆H₄ | H | H | C₆H₅ | |
| 72. | 4-CN—C₆H₄ | H | H | C₆H₅ | |
| 73. | 4-CF₃—C₆H₄ | H | H | C₆H₅ | |
| 74. | 2-Naphthyl | H | H | C₆H₅ | |
| 75. | 3-Naphthyl | H | H | C₆H₅ | |
| 76. | 4-Cl—C₆H₄ | H | H | 2-Cl—C₆H₄ | |
| 77. | 4-CH₃—C₆H₄ | H | H | 3-Cl—C₆H₄ | |
| 78. | 4-OCH₃ | H | H | 4-Cl—C₆H₄ | |
| 79. | 4-NO₂—C₆H₄ | H | H | 2-CH₃—C₆H₄ | |
| 80. | 4-CN—C₆H₄ | H | H | 3-CH₃—C₆H₄ | |
| 81. | 4-CF₃—C₆H₄ | H | H | 4-CH₃—C₆H₄ | |
| 82. | 2-Naphthyl | H | H | 3,4-(Cl)₂—C₆H₃ | |
| 83. | 3-Naphthyl | H | H | 3,4-(Cl)₂—C₆H₃ | |
| 84. | 4-Cl—C₆H₄ | CH₃ | H | C₆H₅ | |
| 85. | 4-CH₃—C₆H₄ | C₂H₅ | H | C₆H₅ | |
| 86. | 4-OCH₃ | C₃H₇ | H | C₆H₅ | |
| 87. | 4-NO₂—C₆H₄ | c-C₃H₅ | H | C₆H₅ | |
| 88. | 4-CN—C₆H₄ | C₄H₉ | H | C₆H₅ | |
| 89. | 4-CF₃—C₆H₄ | CH₃ | H | C₆H₅ | |
| 90. | 2-Naphthyl | C₂H₅ | H | C₆H₅ | |
| 91. | 3-Naphthyl | c-C₃H₅ | H | C₆H₅ | |
| 92. | 4-Cl—C₆H₄ | H | H | CH₂—CH₂—(CH₃O)₂C₆H₃ | 106 |
| 93. | 3,4-(Cl)₂—C₆H₃ | H | H | C₆H₅ | |
| 94. | 2,4-(Cl)₂—C₆H₃ | H | H | C₆H₅ | |
| 95. | 3-Cl—C₆H₄ | H | H | CH₂—CH₂—(CH₃O)₂C₆H₃ | oil |
| 96. | 4-CH₃—C₆H₄ | H | H | CH₂—CH₂—(CH₃O)₂C₆H₃ | 113 |
| 97. | C₆H₅ | H | H | CH₂—CH₂—(CH₃O)₂C₆H₃ | 100 |
| 98. | 2-NO₂—C₆H₄ | c-C₃H₅ | H | C₆H₅ | |
| 99. | 4-F—C₆H₄ | H | H | CH₂—CH₂—(CH₃O)₂C₆H₃ | |
| 100. | 4-CF₃—C₆H₄ | H | H | CH₂—CH₂—(CH₃O)₂C₆H₃ | |
| 101. | 2-Naphthyl | C₂H₅ | H | 2-CH₃—C₆H₅ | |
| 102. | 3-Naphthyl | c-C₃H₅ | H | 2-Cl—C₆H₅ | |
| 103. | 3-CH₃—C₆H₄ | H | H | CH₂—CH₂—(CH₃O)₂C₆H₃ | |
| 104. | 3,4-(Cl)₂—C₆H₃ | CH₃ | H | C₆H₅ | |
| 105. | 3-Cl—C₆H₄ | CH₃ | H | C₆H₅ | |
| 106. | 3-CH₃—C₆H₄ | C₂H₅ | H | C₆H₅ | |
| 107. | 3-OCH₃ | C₃H₇ | H | C₆H₅ | |

TABLE 1-continued

| | Aryl | $R^3$ | $R^2$ | $R^1$ | m.p. |
|---|---|---|---|---|---|
| 108. | 3-NO$_2$—C$_6$H$_4$ | c-C$_3$H$_5$ | H | C$_6$H$_5$ | |
| 109. | 3-CN—C$_6$H$_4$ | C$_4$H$_9$ | H | C$_6$H$_5$ | |
| 110. | 3-CF$_3$—C$_6$H$_4$ | CH$_3$ | H | C$_6$H$_5$ | |
| 111. | 4-Cl—C$_6$H$_4$ | H | H | 2-Cl—C$_6$H$_4$ | 121–122 |
| 112. | 4-Cl—C$_6$H$_4$ | H | H | 3-Cl—C$_6$H$_4$ | 140–141 |
| 113. | 4-Cl—C$_6$H$_4$ | H | H | 4-Cl—C$_6$H$_4$ | 162–163 |
| 114. | 4-Cl—C$_6$H$_4$ | H | H | 2,3-Cl$_2$—C$_6$H$_3$ | |
| 115. | 4-Cl—C$_6$H$_4$ | H | H | 2,4-Cl$_2$—C$_6$H$_3$ | 129–130 |
| 116. | 4-Cl—C$_6$H$_4$ | H | H | 2,5-Cl$_2$—C$_6$H$_3$ | |
| 117. | 4-Cl—C$_6$H$_4$ | H | H | 2,6-Cl$_2$—C$_6$H$_3$ | 213–215 |
| 118. | 4-Cl—C$_6$H$_4$ | H | H | 3,4-Cl$_2$—C$_6$H$_3$ | |
| 119. | 4-Cl—C$_6$H$_4$ | H | H | 3,5-Cl$_2$—C$_6$H$_3$ | 201 |
| 120. | 4-Cl—C$_6$H$_4$ | H | H | 2-CH$_3$—C$_6$H$_4$ | 147–148 |
| 121. | 4-Cl—C$_6$H$_4$ | H | H | 3-CH$_3$—C$_6$H$_4$ | 126–127 |
| 122. | 4-Cl—C$_6$H$_4$ | H | H | 4-CH$_3$—C$_6$H$_4$ | 148–149 |
| 123. | 4-Cl—C$_6$H$_4$ | H | H | 2,3-(CH$_3$)$_2$—C$_6$H$_3$ | 162–163 |
| 124. | 4-Cl—C$_6$H$_4$ | H | H | 2,4-(CH$_3$)$_2$—C$_6$H$_3$ | 175 |
| 125. | 4-Cl—C$_6$H$_4$ | H | H | 2,5-(CH$_3$)$_2$—C$_6$H$_3$ | 185 |
| 126. | 4-Cl—C$_6$H$_4$ | H | H | 2,6-(CH$_3$)$_2$—C$_6$H$_3$ | 200–201 |
| 127. | 4-Cl—C$_6$H$_4$ | H | H | 3,4-(CH$_3$)$_2$—C$_6$H$_3$ | |
| 128. | 4-Cl—C$_6$H$_4$ | H | H | 3,5-(CH$_3$)$_2$—C$_6$H$_3$ | 190–191 |
| 129. | 4-Cl—C$_6$H$_4$ | H | H | 4-CH$_3$O—C$_6$H$_4$ | 127–130 |
| 130. | 4-Cl—C$_6$H$_4$ | H | H | 4-F—C$_6$H$_4$ | |
| 131. | 4-Cl—C$_6$H$_4$ | H | H | 4-CN—C$_6$H$_4$ | 110 |
| 132. | 4-Cl—C$_6$H$_4$ | H | H | 4-CF$_3$—C$_6$H$_4$ | 168 |
| 133. | 4-CH$_3$—C$_6$H$_4$ | H | H | 2-Cl—C$_6$H$_4$ | 115 |
| 134. | 4-CH$_3$—C$_6$H$_4$ | H | H | 3-Cl—C$_6$H$_4$ | 137 |
| 135. | 4-CH$_3$—C$_6$H$_4$ | H | H | 4-Cl—C$_6$H$_4$ | 113 |
| 136. | 4-CH$_3$—C$_6$H$_4$ | H | H | 2,3-Cl$_2$—C$_6$H$_3$ | |
| 137. | 4-CH$_3$—C$_6$H$_4$ | H | H | 2,4-Cl$_2$—C$_6$H$_3$ | 146 |
| 138. | 4-CH$_3$—C$_6$H$_4$ | H | H | 2,5-Cl$_2$—C$_6$H$_3$ | |
| 139. | 4-CH$_3$—C$_6$H$_4$ | H | H | 2,6-Cl$_2$—C$_6$H$_3$ | |
| 140. | 4-CH$_3$—C$_6$H$_4$ | H | H | 3,4-Cl$_2$—C$_6$H$_3$ | |
| 141. | 4-CH$_3$—C$_6$H$_4$ | H | H | 3,5-Cl$_2$—C$_6$H$_3$ | 199–201 |
| 142. | 4-CH$_3$—C$_6$H$_4$ | H | H | 2-CH$_3$—C$_6$H$_4$ | 158–159 |
| 143. | 4-CH$_3$—C$_6$H$_4$ | H | H | 3-CH$_3$—C$_6$H$_4$ | 116–117 |
| 144. | 4-CH$_3$—C$_6$H$_4$ | H | H | 4-CH$_3$—C$_6$H$_4$ | |
| 145. | 4-CH$_3$—C$_6$H$_4$ | H | H | 2,3-(CH$_3$)$_2$—C$_6$H$_3$ | |
| 146. | 4-CH$_3$—C$_6$H$_4$ | H | H | 2,4-(CH$_3$)$_2$—C$_6$H$_3$ | |
| 147. | 4-CH$_3$—C$_6$H$_4$ | H | H | 2,5-(CH$_3$)$_2$—C$_6$H$_3$ | 148–149 |
| 148. | 4-CH$_3$—C$_6$H$_4$ | H | H | 2,6-(CH$_3$)$_2$—C$_6$H$_3$ | 181–182 |
| 149. | 4-CH$_3$—C$_6$H$_4$ | H | H | 3,4-(CH$_3$)$_2$—C$_6$H$_3$ | |
| 150. | 4-CH$_3$—C$_6$H$_4$ | H | H | 3,5-(CH$_3$)$_2$—C$_6$H$_3$ | 157–158 |
| 151. | 4-CH$_3$—C$_6$H$_4$ | H | H | 4-CH$_3$O—C$_6$H$_4$ | |
| 152. | 4-CH$_3$—C$_6$H$_4$ | H | H | 4-F—C$_6$H$_4$ | 166–167 |
| 153. | 4-CH$_3$—C$_6$H$_4$ | H | H | 4-CN—C$_6$H$_4$ | |
| 154. | 4-CH$_3$—C$_6$H$_4$ | H | H | 4-CF$_3$—C$_6$H$_4$ | |
| 155. | C$_6$H$_5$ | CH$_3$ | H | 2,4-Cl$_2$—C$_6$H$_3$ | oil |
| 156. | C$_6$H$_5$ | CH$_3$ | H | 2,4-(CH$_3$)$_2$—C$_6$H$_3$ | 82–83 |
| 157. | C$_6$H$_5$ | CH$_3$ | H | 2,4-(CH$_3$O)$_2$—C$_6$H$_3$ | oil |
| 158. | C$_6$H$_5$ | CH$_3$ | H | | |
| 159. | C$_6$H$_5$ | CH$_3$ | H | | |
| 160. | C$_6$H$_5$ | i-C$_3$H$_7$ | H | 2,4-(CH$_3$O)$_2$—C$_6$H$_3$ | oil |
| 161. | C$_6$H$_5$ | i-C$_3$H$_7$ | H | 2-CH$_3$—C$_6$H$_4$ | 102 |
| 162. | C$_6$H$_5$ | i-C$_3$H$_7$ | H | 4-CH$_3$—C$_6$H$_4$ | oil |
| 163. | C$_6$H$_5$ | i-C$_3$H$_7$ | H | 2,4-CH$_3$—C$_6$H$_3$ | 118–119 |
| 164. | C$_6$H$_5$ | i-C$_3$H$_7$ | H | 2-CH$_3$O—C$_6$H$_4$ | oil |
| 165. | C$_6$H$_5$ | i-C$_3$H$_7$ | H | 4-CH$_3$O—C$_6$H$_4$ | oil |
| 166. | C$_6$H$_5$ | i-C$_3$H$_7$ | H | 2-CN—C$_6$H$_4$ | oil |
| 167. | C$_6$H$_5$ | i-C$_3$H$_7$ | H | 4-CN—C$_6$H$_4$ | oil |
| 168. | C$_6$H$_5$ | C$_2$H$_5$ | H | 2-Cl—C$_6$H$_4$ | oil |
| 169. | C$_6$H$_5$ | C$_2$H$_5$ | H | 4-Cl—C$_6$H$_4$ | 106 |
| 170. | C$_6$H$_5$ | C$_2$H$_5$ | H | 2-CH$_3$—C$_6$H$_4$ | oil |
| 171. | C$_6$H$_5$ | C$_2$H$_5$ | H | 4-CH$_3$—C$_6$H$_4$ | 93–94 |
| 172. | 4-CH$_3$—C$_6$H$_4$ | CH$_3$ | H | 2-Cl—C$_6$H$_4$ | oil |
| 173. | C$_6$H$_5$ | C$_2$H$_5$ | H | 2,4-Cl$_2$—C$_6$H$_3$ | oil |
| 174. | C$_6$H$_5$ | C$_2$H$_5$ | H | 2,4-(CH$_3$)$_2$—C$_6$H$_3$ | oil |
| 175. | C$_6$H$_5$ | C$_2$H$_5$ | H | 2-CH$_3$O—C$_6$H$_4$ | oil |
| 176. | C$_6$H$_5$ | C$_2$H$_5$ | H | 4-CH$_3$O—C$_6$H$_4$ | oil |
| 177. | C$_6$H$_5$ | C$_2$H$_5$ | H | 2,4-(CH$_3$O)$_2$—C$_6$H$_3$ | oil |
| 178. | C$_6$H$_5$ | C$_2$H$_5$ | H | 2-CN—C$_6$H$_4$ | oil |
| 179. | C$_6$H$_5$ | C$_2$H$_5$ | H | 4-CN—C$_6$H$_4$ | oil |
| 180. | 4-CH$_3$—C$_6$H$_4$ | CH$_3$ | H | 4-Cl—C$_6$H$_4$ | 82 |
| 181. | 4-CH$_3$—C$_6$H$_4$ | CH$_3$ | H | 2-CH$_3$—C$_6$H$_4$ | 75–76 |
| 182. | 4-CH$_3$—C$_6$H$_4$ | CH$_3$ | H | 4-CH$_3$—C$_6$H$_4$ | oil |
| 183. | 4-CH$_3$—C$_6$H$_4$ | CH$_3$ | H | 2,4-Cl$_2$—C$_6$H$_3$ | 122–124 |
| 184. | 4-CH$_3$—C$_6$H$_4$ | CH$_3$ | H | 2,4-(CH$_3$)$_2$—C$_6$H$_3$ | 120–121 |

TABLE 1-continued

| | Aryl | R³ | R² | R¹ | m.p. |
|---|---|---|---|---|---|
| 185. | 4-CH₃—C₆H₄ | CH₃ | H | 2-CH₃O—C₆H₄ | oil |
| 186. | 4-CH₃—C₆H₄ | CH₃ | H | 4-CH₃O—C₆H₄ | oil |
| 187. | 4-CH₃—C₆H₄ | CH₃ | H | 2,4-(CH₃O)₂—C₆H₃ | oil |
| 188. | 4-CH₃—C₆H₄ | CH₃ | H | 2-CN—C₆H₄ | 130–132 |
| 189. | 4-CH₃—C₆H₄ | CH₃ | H | 4-CN—C₆H₄ | oil |
| 190. | C₆H₅ | i-C₃H₇ | H | 2-Cl—C₆H₄ | oil |
| 191. | 4-Cl—C₆H₄ | H | H | 2-CN—C₆H₄ | 141–142 |
| 192. | 4-Cl—C₆H₄ | H | H | 2-OCH₃—C₆H₄ | 139 |
| 193. | 4-Cl—C₆H₄ | H | H | 2,4-(CH₃O)₂—C₆H₃ | 177 |
| 194. | 4-CN—C₆H₄ | H | H | 2,4-(CH₃)₂—C₆H₃ | 168–169 |
| 195. | 4-CN—C₆H₄ | H | H | 2,4-(Cl)₂—C₆H₃ | 189 |
| 196. | 4-CN—C₆H₄ | H | H | 4-CN—C₆H₃ | 187 |
| 197. | 4-CN—C₆H₄ | H | H | 4-Cl—C₆H₃ | 204 |
| 198. | 4-CN—C₆H₄ | H | H | 4-CH₃—C₆H₃ | 149 |
| 199. | 4-CN—C₆H₄ | H | H | 4-OCH₃—C₆H₃ | 149 |
| 200. | 4-CN—C₆H₄ | H | H | 2,4-(CH₃O)₂—C₆H₃ | 165 |
| 201. | 4-CN—C₆H₄ | H | H | 2-Cl—C₆H₄ | 158 |
| 202. | 4-CN—C₆H₄ | H | H | 2-CH₃—C₆H₄ | 164 |
| 203. | 4-CN—C₆H₄ | H | H | 2-OCH₃—C₆H₄ | 60–66 |
| 204. | 4-CH₃O—C₆H₄ | H | H | 2-CH₃—C₆H₄ | 171–176 |
| 205. | 4-CH₃O—C₆H₄ | H | H | 4-Cl—C₆H₄ | 151–155 |
| 206. | 4-CH₃O—C₆H₄ | H | H | 4-CH₃—C₆H₄ | 130–132 |
| 207. | 4-CH₃O—C₆H₄ | H | H | 2,4-(CH₃)₂—C₆H₃ | 138–140 |
| 208. | 4-CH₃—C₆H₄ | i-C₃H₇ | H | 4-tBu-C₆H₄ | 134–136 |
| 209. | 4-CH₃—C₆H₄ | i-C₃H₇ | H | 4-i-C₃H₇-C₆H₄ | 102–104 |
| 210. | 4-CH₃—C₆H₄ | i-C₃H₇ | H | 4-F—C₆H₄ | oil |
| 211. | 4-CH₃—C₆H₄ | i-C₃H₇ | H | 2-F—C₆H₄ | 80–81 |
| 212. | 4-CH₃—C₆H₄ | i-C₃H₇ | H | 4-CN—C₆H₄ | 83 |
| 213. | 4-CH₃—C₆H₄ | i-C₃H₇ | H | 2-CN—C₆H₄ | oil |
| 214. | 4-CH₃—C₆H₄ | i-C₃H₇ | H | 2,4-(CH₃O)₂—C₆H₃ | oil |
| 215. | 4-CH₃—C₆H₄ | i-C₃H₇ | H | 4-OCH₃—C₆H₄ | oil |
| 216. | 4-CH₃—C₆H₄ | i-C₃H₇ | H | 2-OCH₃—C₆H₄ | 84–85 |
| 217. | 4-CH₃—C₆H₄ | i-C₃H₇ | H | 2,4-(CH₃)₂—C₆H₃ | 99 |
| 218. | 4-CH₃—C₆H₄ | i-C₃H₇ | H | 2,4-(Cl)₂—C₆H₃ | oil |
| 219. | 4-CH₃—C₆H₄ | i-C₃H₇ | H | 4-CH₃—C₆H₄ | 96–97 |
| 220. | 4-CH₃—C₆H₄ | i-C₃H₇ | H | 2-CH₃—C₆H₄ | 133–135 |
| 221. | 4-CH₃—C₆H₄ | i-C₃H₇ | H | 4-Cl—C₆H₄ | 98–99 |
| 222. | 4-CH₃—C₆H₄ | i-C₃H₇ | H | 2-Cl—C₆H₄ | oil |
| 223. | 3-Cl—C₆H₄ | H | H | 2-Cl—C₆H₄ | 113–114 |
| 224. | 3-Cl—C₆H₄ | H | H | 4-Cl—C₆H₄ | 122–124 |
| 225. | 3-Cl—C₆H₄ | H | H | 2-CH₃—C₆H₄ | 142–143 |
| 226. | 3-Cl—C₆H₄ | H | H | 4-CH₃—C₆H₄ | 114 |
| 227. | 3-Cl—C₆H₄ | H | H | 2,4-(Cl)₂—C₆H₃ | 143 |
| 228. | 3-Cl—C₆H₄ | H | H | 2,4-(CH₃)₂—C₆H₃ | 118–119 |
| 229. | 3-Cl—C₆H₄ | H | H | 2-CH₃O—C₆H₄ | 102 |
| 230. | 3-Cl—C₆H₄ | H | H | 4-CH₃O—C₆H₄ | 138 |
| 231. | 3-Cl—C₆H₄ | H | H | 2,4-(CH₃O)₂—C₆H₄ | 118–119 |
| 232. | 3-Cl—C₆H₄ | H | H | 4-CN—C₆H₄ | 47–55 |
| 233. | 3-Cl—C₆H₄ | H | H | 2-F—C₆H₄ | 128–131 |
| 234. | 3-Cl—C₆H₄ | H | H | 4-F—C₆H₄ | 132–133 |
| 235. | 3-Cl—C₆H₄ | H | H | 4-i-C₃H₇-C₆H₄ | 131–133 |
| 236. | 3-Cl—C₆H₄ | H | H | 4-t-C₄H₉-C₆H₄ | 123–125 |
| 237. | 4-CH₃O—C₆H₄ | H | H | 2,4-(Cl)₂—C₆H₃ | 132 |
| 238. | 4-CH₃O—C₆H₄ | H | H | 2,4-(CH₃O)₂—C₆H₃ | 115–118 |
| 239. | 4-CH₃O—C₆H₄ | H | H | 2-CH₃O—C₆H₄ | 130 |
| 240. | 4-CH₃O—C₆H₄ | H | H | 2-CN—C₆H₄ | 138–139 |
| 241. | 4-CH₃O—C₆H₄ | H | H | 4-CH₃O—C₆H₄ | 142–143 |
| 242. | 4-CH₃O—C₆H₄ | H | H | 4-CN—C₆H₄ | 128–129 |
| 243. | 4-CH₃O—C₆H₄ | H | H | 2-F—C₆H₄ | 132 |
| 244. | 4-CH₃O—C₆H₄ | H | H | 2-Cl—C₆H₄ | 120–121 |
| 245. | 4-Cl—C₆H₄ | H | H | 2-F—C₆H₄ | 126–127 |
| 246. | 4-CN—C₆H₄ | H | H | 2-F—C₆H₄ | 146–147 |
| 247. | 4-Cl—C₆H₄ | H | H | 4-i-C₃H₇—C₆H₄ | 148–149 |
| 248. | 4-Cl-C₆H₄ | H | H | 4-t-C₄H₉—C₆H₄ | 161–162 |
| 249. | 4-CN—C₆H₄ | H | H | 4-F—C₆H₄ | 183–185 |
| 250. | 4-CN—C₆H₄ | H | H | 4-i-C₃H₇—C₆H₄ | 140–149 |
| 251. | 4-CN—C₆H₄ | H | H | 4-t-Bu-C₆H₄ | 89–93 |
| 252. | 4-CH₃O—C₆H₄ | H | H | 4-F—C₆H₄ | 127–128 |
| 253. | 4-CH₃O—C₆H₄ | H | H | 4-i-C₃H₇—C₆H₄ | 106–110 |
| 254. | 4-CH₃—C₆H₄ | C₂H₅ | H | 2-Cl—C₆H₄ | oil |
| 255. | 4-CH₃—C₆H₄ | C₂H₅ | H | 2,4-(Cl)₂—C₆H₃ | oil |
| 256. | 4-CH₃—C₆H₄ | C₂H₅ | H | 2,4-(CH₃)₂—C₆H₃ | 90–92 |
| 257. | 4-CH₃—C₆H₄ | C₂H₅ | H | 2,4-(CH₃O)₂—C₆H₃ | oil |
| 258. | 4-CH₃—C₆H₄ | C₂H₅ | H | 4-Cl—C₆H₄ | 95–96 |
| 259. | 4-CH₃—C₆H₄ | C₂H₅ | H | 2-CH₃—C₆H₄ | 89–90 |
| 260. | 4-CH₃—C₆H₄ | C₂H₅ | H | 4-CH₃—C₆H₄ | 92–94 |
| 261. | 4-CH₃—C₆H₄ | C₂H₅ | H | 2-CH₃O—C₆H₄ | oil |

TABLE 1-continued

| | Aryl | R³ | R² | R¹ | m.p. |
|---|---|---|---|---|---|
| 262. | 4-CH₃—C₆H₄ | C₂H₅ | H | 4-CH₃O—C₆H₄ | oil |
| 263. | 4-CH₃—C₆H₄ | C₂H₅ | H | 2-CN—C₆H₄ | 133–135 |
| 264. | 4-CH₃—C₆H₄ | C₂H₅ | H | 4-CN—C₆H₄ | 135–136 |
| 265. | 4-CH₃—C₆H₄ | C₂H₅ | H | 2-F—C₆H₄ | oil |
| 266. | 4-CH₃—C₆H₄ | C₂H₅ | H | 4-F—C₆H₄ | oil |
| 267. | 4-CH₃—C₆H₄ | C₂H₅ | H | 4-i-C₃H₇—C₆H₄ | oil |
| 268. | 4-CH₃—C₆H₄ | C₂H₅ | H | 4-t-Bu-C₆H₄ | 105 |
| 269. | 4-CH₃Ol—C₆H₄ | C₂H₅ | H | 4-t-Bu-C₆H₄ | 65–67 |
| 270. | 4-Cl—C₆H₄ | C₂H₅ | H | 2-CH₃—C₆H₄ | 96–97 |
| 271. | 4-Cl—C₆H₄ | C₂H₅ | H | 4-Cl—C₆H₄ | 128 |
| 272. | 4-Cl—C₆H₄ | C₂H₅ | H | 4-CH₃—C₆H₄ | 87–88 |
| 273. | 4-Cl—C₆H₄ | C₂H₅ | H | 2,4-(Cl)₂—C₆H₃ | oil |
| 274. | 4-Cl—C₆H₄ | C₂H₅ | H | 2,4-(CH₃)₂—C₆H₃ | 112 |
| 275. | 4-Cl—C₆H₄ | C₂H₅ | H | 2-CH₃O—C₆H₄ | oil |
| 276. | 4-Cl—C₆H₄ | C₂H₅ | H | 4-CH₃O—C₆H₄ | 90–92 |
| 277. | 4-Cl—C₆H₄ | C₂H₅ | H | 2,4-(CH₃O)₂—C₆H₃ | oil |
| 278. | 4-Cl—C₆H₄ | C₂H₅ | H | 4-CN—C₆H₄ | 154 |
| 279. | 3-CH₃—C₆H₄ | H | H | 2-Cl—C₆H₄ | 71 |
| 280. | 3-CH₃—C₆H₄ | H | H | 4-Cl—C₆H₄ | 117 |
| 281. | 3-CH₃—C₆H₄ | H | H | 2-CH₃—C₆H₄ | 107–109 |
| 282. | 3-CH₃—C₆H₄ | H | H | 4-CH₃—C₆H₄ | 112–113 |
| 283. | 3-CH₃—C₆H₄ | H | H | 2,4-(Cl)₂—C₆H₃ | 100–102 |
| 284. | 3-CH₃—C₆H₄ | H | H | 2,4-(CH₃)₂—C₆H₃ | 124–126 |
| 285. | 3-CH₃—C₆H₄ | H | H | 2,4-(CH₃O)₂—C₆H₃ | 102 |
| 286. | 3-CH₃—C₆H₄ | H | H | 2-CH₃O—C₆H₄ | 124–125 |
| 287. | 3-CH₃—C₆H₄ | H | H | 4-CH₃O—C₆H₄ | 105–107 |
| 288. | 3-CH₃—C₆H₄ | H | H | 2-CN—C₆H₄ | 94–98 |
| 289. | 3-CH₃—C₆H₄ | H | H | 4-CN—C₆H₄ | 89–90 |
| 290. | 3-CH₃—C₆H₄ | H | H | 2-F—C₆H₄ | 100–101 |
| 291. | 3-CH₃—C₆H₄ | H | H | 4-F—C₆H₄ | 91–93 |
| 292. | 3-CH₃—C₆H₄ | H | H | 4-C₃H₇—C₆H₄ | 93–94 |
| 293. | 3-CH₃—C₆H₄ | H | H | 4-t-C₄H₉—C₆H₄ | 77–79 |
| 294. | 3-CH₃—C₆H₄ | H | H | 3,4-(Cl)₂—C₆H₃ | 134–136 |
| 295. | 3-CH₃—C₆H₄ | H | H | 3,4-(CH₃)₂—C₆H₃ | 123–125 |
| 296. | 3-CH₃—C₆H₄ | H | H | 3,4-(F)₂—C₆H₃ | 109–110 |
| 297. | 3-CH₃—C₆H₄ | H | H | 3,4-(CH₃O)₂—C₆H₃ | oil |
| 298. | 3-Cl—C₆H₄ | H | H | 3,4-(F)₂—C₆H₃ | 133–134 |
| 299. | 3-Cl—C₆H₄ | H | H | 3,4-(CH₃O)₂—C₆H₃ | 192–193 |
| 300. | 3-Cl—C₆H₄ | H | H | 3,4-(Cl)₂—C₆H₃ | 177 |
| 301. | 3-Cl—C₆H₄ | H | H | 3,4-(CH₃)₂—C₆H₃ | 97 |
| 302. | 4-Cl—C₆H₄ | H | H | 3,4-(Cl)₂—C₆H₃ | 213–214 |
| 303. | 4-Cl—C₆H₄ | H | H | 3,4-(CH₃)₂—C₆H₃ | 153–154 |
| 304. | 4-Cl—C₆H₄ | H | H | 3,4-(F)₂—C₆H₃ | 150–151 |
| 305. | 4-Cl—C₆H₄ | H | H | 3,4-(CH₃O)₂—C₆H₃ | 167 |
| 306. | 4-CN—C₆H₄ | H | H | 3,4-(F)₂—C₆H₃ | 178–179 |
| 307. | 4-CN—C₆H₄ | H | H | 3,4-(CH₃)₂—C₆H₃ | 144 |
| 308. | 4-CN—C₆H₄ | H | H | 3,4-(CH₃O)₂—C₆H₃ | |
| 309. | 4-CN—C₆H₄ | H | H | 3,4-(Cl)₂—C₆H₃ | 260 |
| 310. | 4-CH₃O—C₆H₄ | H | H | 3,4-(Cl)₂—C₆H₃ | 162–163 |
| 311. | 4-CH₃O—C₆H₄ | H | H | 3,4-(CH₃)₂—C₆H₃ | 122–123 |
| 312. | 4-CH₃O—C₆H₄ | H | H | 3,4-(F)₂—C₆H₃ | 148 |
| 313. | 4-Cl—C₆H₄ | C₂H₅ | H | 2-Cl—C₆H₄ | oil |
| 314. | 4-Cl—C₆H₄ | i-C₃H₇ | H | 2,4-(Cl)₂—C₆H₃ | 113 |
| 315. | 4-Cl—C₆H₄ | i-C₃H₇ | H | 2,4-(CH₃O)₂—C₆H₃ | oil |
| 316. | 4-Cl—C₆H₄ | i-C₃H₇ | H | 2,4-(CH₃)₂—C₆H₃ | 118 |
| 317. | 4-Cl—C₆H₄ | i-C₃H₇ | H | 2-Cl—C₆H₄ | oil |
| 318. | 4-Cl—C₆H₄ | i-C₃H₇ | H | 3-Cl—C₆H₄ | 110–111 |
| 319. | 4-Cl—C₆H₄ | i-C₃H₇ | H | 4-Cl—C₆H₄ | 126 |
| 320. | 4-Cl—C₆H₄ | i-C₃H₇ | H | 2-CH₃—C₆H₄ | 138 |
| 321. | 4-Cl—C₆H₄ | i-C₃H₇ | H | 4-CH₃—C₆H₄ | 95–96 |
| 322. | 4-Cl—C₆H₄ | i-C₃H₇ | H | 4-CN—C₆H₄ | 167–168 |
| 323. | 4-Cl—C₆H₄ | i-C₃H₇ | H | 2-CN—C₆H₄ | 109 |
| 324. | 4-Cl—C₆H₄ | i-C₃H₇ | H | 4-CH₃O—C₆H₄ | oil |
| 325. | 3-CF₃—C₆H₄ | H | H | 2-Cl—C₆H₄ | 93–95 |
| 326. | 3-CF₃—C₆H₄ | H | H | 4-Cl—C₆H₄ | 166–167 |
| 327. | 3-CF₃—C₆H₄ | H | H | 2-CH₃—C₆H₄ | 141–142 |
| 328. | 3-CF₃—C₆H₄ | H | H | 4-CH₃—C₆H₄ | 144–146 |
| 329. | 3-CF₃—C₆H₄ | H | H | 2-CH₃O—C₆H₄ | oil |
| 330. | 3-CF₃—C₆H₄ | H | H | 4-CH₃O—6H₄ | 138 |
| 331. | 3-CF₃—C₆H₄ | H | H | 4-CN—C₆H₄ | 122 |
| 332. | 3-CF₃—C₆H₄ | H | H | 2-F—C₆H₄ | 85–86 |
| 333. | 3-CF₃—C₆H₄ | H | H | 4-F—C₆H₄ | 133–134 |
| 334. | 3-CF₃—C₆H₄ | H | H | 4-i-C₃H₇—C₆H₄ | 127–128 |
| 335. | 3-CF₃—C₆H₄ | H | H | 4-t-C₄H₉—C₆H₄ | 133–134 |
| 336. | 3-CF₃—C₆H₄ | H | H | 3,4-(Cl)₂—C₆H₃ | 178–179 |
| 337. | 3-CF₃—C₆H₄ | H | H | 3,4-(CH₃)₂—C₆H₃ | 116 |
| 338. | 3-CF₃—C₆H₄ | H | H | 3,4-(F)₂—C₆H₃ | 110 |

TABLE 1-continued

| | Aryl | R³ | R² | R¹ | m.p. |
|---|---|---|---|---|---|
| 339. | 3-CF$_3$—C$_6$H$_4$ | H | H | 2,4-(CH$_3$)$_2$—C$_6$H$_3$ | 95–96 |
| 340. | 3-CF$_3$—C$_6$H$_4$ | H | H | 2,4-(Cl)$_2$—C$_6$H$_3$ | 120 |
| 341. | 3-CF$_3$—C$_6$H$_4$ | H | H | 3,4-(CH$_3$O)$_2$—C$_6$H$_3$ | 144 |
| 342. | 3-CF$_3$—C$_6$H$_4$ | H | H | 2,4-(CH$_3$O)$_2$—C$_6$H$_3$ | 125 |
| 343. | 3,5-(Cl)$_2$C$_6$H$_3$ | H | H | 2-Cl—C$_6$H$_4$ | 160 |
| 344. | 3,5-(Cl)$_2$C$_6$H$_3$ | H | H | 4-Cl—C$_6$H$_4$ | 214 |
| 345. | 3,5-(Cl)$_2$C$_6$H$_3$ | H | H | 2-CH$_3$—C$_6$H$_4$ | 180–182 |
| 346. | 3,5-(Cl)$_2$C$_6$H$_3$ | H | H | 4-CH$_3$—C$_6$H$_4$ | 166 |
| 347. | 3,5-(Cl)$_2$C$_6$H$_3$ | H | H | 2-CH$_3$O—C$_6$H$_4$ | 164 |
| 348. | 3,5-(Cl)$_2$C$_6$H$_3$ | H | H | 4-CH$_3$O—C$_6$H$_4$ | 181 |
| 349. | 3,5-(Cl)$_2$C$_6$H$_3$ | H | H | 2-F—C$_6$H$_4$ | 169 |
| 350. | 3,5-(Cl)$_2$C$_6$H$_3$ | H | H | 4-CN—C$_6$H$_4$ | 160 |
| 351. | 3,5-(Cl)$_2$C$_6$H$_3$ | H | H | 4-F—C$_6$H$_4$ | 164 |
| 352. | 3,5-(Cl)$_2$C$_6$H$_3$ | H | H | 4-i-C$_3$H$_7$—C$_6$H$_4$ | oil |
| 353. | 3,5-(Cl)$_2$C$_6$H$_3$ | H | H | 4-t-C$_4$H$_9$—C$_6$H$_4$ | 158–160 |
| 354. | 3,5-(Cl)$_2$C$_6$H$_3$ | H | H | 2,4-(Cl)$_2$—C$_6$H$_3$ | 153–155 |
| 355. | 3,5-(Cl)$_2$C$_6$H$_3$ | H | H | 2,4-(CH$_3$)$_2$—C$_6$H$_3$ | 205 |
| 356. | 3,5-(Cl)$_2$C$_6$H$_3$ | H | H | 2,4-(CH$_3$O)$_2$—C$_6$H$_3$ | 175 |
| 357. | 3,5-(Cl)$_2$C$_6$H$_3$ | H | H | 3,4-(Cl)$_2$—C$_6$H$_3$ | 226–229 |
| 358. | 3,5-(Cl)$_2$C$_6$H$_3$ | H | H | 3,4-(CH$_3$)$_2$—C$_6$H$_3$ | 145 |
| 359. | 3,5-(Cl)$_2$C$_6$H$_3$ | H | H | 3,4-(F)$_2$—C$_6$H$_3$ | oil |
| 360. | 3,5-(Cl)$_2$C$_6$H$_3$ | H | H | 3,4-(CH$_3$O)$_2$—C$_6$H$_3$ | oil |

The compounds of the formula I can be prepared analogously to the process as described in the literature (cf. DD 156663, J.Am.Chem.Soc. 39 (1908), 63). The synthesis is carried out, for example, by the following standard process, where the phenyl rings in formula II or III may be unsubstituted or substituted:

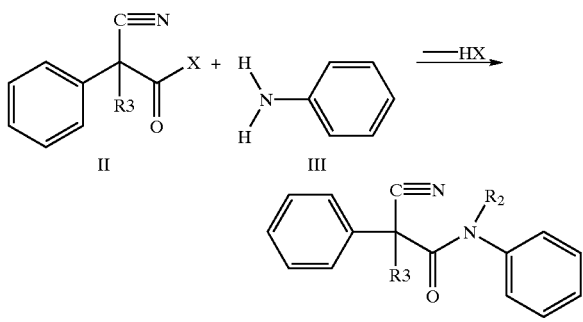

X is a suitable leaving group, such as, for example, halogen or alkoxy.

The cyanocarboxylic acid derivatives of the formula II can be prepared by processes known from the literature (cf. Org. Synthesis, Collect Vol IV, 1963, p. 461 ff.). The phenylamines of the formula III are either commercially available, or they can also be prepared by processes known from the literature.

The compounds of the formula I are suitable for use as active compounds for preparing crop protection compositions. For the purpose of the present invention, crop protection compositions are generally understood as being mixtures of active compounds of the formula I with additives or auxiliaries which make possible the use of the mixtures in agriculture or gardening and the application of these compositions onto areas free from crops or for treating plants. The crop protection compositions can preferably be employed as herbicides and/or fungicides.

The plants are usually sprayed or dusted with the active compounds or the crop protection compositions, or the seeds of the plants are treated with the active compounds.

The compounds of the formula I and their agriculturally useful salts are suitable, both in the form of stereoisomeric mixtures and in the form of the pure stereoisomers, especially as herbicides. The herbicidal compositions comprising the compounds of the formula I control plant growth on non-crop areas very efficiently, especially at high rates of application. They act against broad-leaved weeds and grass weeds in crops such as wheat, rice, maize, soybean and cotton without causing any significant damage to the crop plants. This effect is mainly observed at low rates of application.

Depending on the particular application method, the compounds of the formula I or the compositions comprising them can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum,(Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.

In addition, the compounds of the formula I can also be used in crops which tolerate the action of herbicides owing to breeding, including genetic engineering methods.

The compounds of the formula I or the compositions comprising them can be used, for example, in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, broadcasting or watering. The use forms depend on the intended aims; in any case, they should ensure the finest possible distribution of the active compounds according to the invention.

The herbicidal compositions comprise a herbicidally effective amount of at least one compound of the formula I or an agriculturally useful salt of I and auxiliaries which are customary for formulating crop protection agents.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols, such as methanol, ethanol, propanol, butanol, cyclohexanol, ketones such as cyclohexanone, or strongly polar solvents, for example amines such as N-methylpyrrolidone, or water.

Aqueous use forms can be prepared from emulsion concentrates, suspensions, pastes, wettable powders or water-dispersible granules by adding water. To prepare emulsions, pastes or oil dispersions, the compounds of the formula I, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, for example ligno-, phenol-, naphthalene- and dibutylnapthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates or sulfonated naphthalene and its derivatives with formaldehyde, condensates of naphthalene, or of the naphthalene sulfonic acids with phenol and formaldehyde, polyoxyethylene octyl phenol ether, ethoxylated isooctyl-, octyl- or nonylphenol, alkylphenol or tributylphenyl polyglycol ether, alkylaryl polyether alcohols, isotridecyl alcohol, fatty alcohol ethylene oxide condensates, ethoxylated castor oil, polyoxyethylene alkyl ether or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or jointly grinding the active substances together with a solid carrier.

Granules, for example coated granules, impregnated granules and homogeneous granules, can be prepared by binding the active compounds to solid carriers. Solid carriers are mineral earth, such as silicas, silica gels, silicates, talc, kaolin, limestone, lime, chalk, bowl, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The concentrations of the compounds of the formula I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

The compounds I according to the invention can be formulated, for example, as follows:

a) 20 parts by weight of a compound I are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound.

b) 20 parts by weight of a compound I are dissolved in a mixture composed of 40 parts by weight of cyclohexanone, 30 parts by weight is isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound.

c) 20 parts by weight of a compound I are dissolved in a mixture composed of 25 parts by weight of cyclohexanone, 65 parts by weight of a mineral oil fraction of boiling point 210 to 2800C and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound.

d) 20 parts by weight of a compound I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20000 parts by weight of water gives a spray mixture which comprises 0.1% by weight of the active compound.

e) 3 parts by weight of a compound I are mixed with 97 parts by weight of finely divided kaolin. This gives a dust which comprises 3% by weight of active compound.

f) 20 parts by weight of a compound I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

g) 1 part by weight of a compound I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

h) 1 part by weight of a compound I is dissolved in a mixture composed of 80 parts by weight of cyclohexanone and 20 parts by weight of Wettol® EM 31 (nonionic emulsifier based on ethoxylated castor oil). This gives a stable emulsion concentrate.

The active compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

To widen the spectrum of action and to achieve synergistic effects, the compounds of the formula I may be mixed with a large number of representatives of other herbicidal or growth-regulating groups of active compounds and then applied concomitantly. Suitable components for mixtures are, for example, 1,2,4-thiadiazoles, 1,3,4-thiadiazoles, amides, aminophosphoric acid and its derivatives, aminotriazoles, anilides, aryloxy/hetaryloxyalkanoic acid and its derivatives, benzoic acid and its derivatives, benzothiadiazinones, 2-(aroyl/hetaroyl)-1,3-cyclohexanediones, hetaryl aryl ketones, benzylisoxazolidinones, meta-$CF_3$-phenyl derivatives, carbamates, quinoline carboxylic acid and its derivatives, chloroacetanilides, cyclohexenenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenyl acetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonyl ureas, triazines, triazinones, triazolinones, triazolecarboxamides and uracils.

It may furthermore be advantageous to apply the compounds of the formula I, alone or in combination with other herbicides, in the form of a mixture with other crop protection agents, for example together with agents for controlling pests of phytopathogenic fungi or bacteria. Also of interest is the miscibility with mineral salt solutions, which are employed for treating nutritional and trace element deficiencies. Non-phytotoxic oils and oil concentrates may also be added.

Depending on the control target, the season, the target plant and the growth stage, the active compound application rates are from 0.001 to 3.0, preferably from 0.01 to 1.0, kg of active substance (a. S.)/ha.

Compounds of the formula I also have fungicidal action. They are distinguished, in particular, by excellent action against a broad spectrum of phytopathogenic fungi, especially from the classes of the Ascomycetes, Deuteromycetes, Phycomycetes and Basidiomycetes. Some of them act systemically, and they can therefore also be employed as folia- and soil-acting fungicides.

They are of particular importance for controlling a large number of fungi in various crop plants, such as wheat, rye, barley, oats, rice, maize, turf, cotton, soybean, coffee, sugarcane, grapevines, fruits and ornamental plants and vegetables, such as cucumbers, beans and cucurbits, and in the seeds of these plants.

The compounds are applied by treating the fungi or the seeds, plants, materials or the soil to be protected against fungal attack with a fungicidally active amount of the active compounds. Application is carried out before or after the infection of the materials, plants or seeds by the fungi.

The novel compounds are particularly suitable for controlling the following plant diseases: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton and turf, Ustilago species in cereals and sugarcane, *Venturia inaequalis* (scab) in apples, Helminthosporium species in cereals, *Septoria nodorum* in wheat, *Botrytis cinerea* (gray mold) in strawberries, grapevines, ornamental plants and vegetables, *Cercospora arachidicola* in groundnuts, *Pseudocercosporella herpotrichoides* in wheat, barley, *Pyricularia oryzae* in rice, Phytophthora infestans in potatoes and tomatoes, Fusarium and Verticillium species in a variety of plants, *Plasmopara viticola* in grapevines, Alternaria species in vegetables and fruit.

The active compounds of the formula I can also be employed in the protection of materials (wood protection), for example against *Paecilomyces variotii*.

The fungicidal compositions generally comprise between 0.1 and 95, preferably between 0.5 and 90, % by weight of active compound.

Depending on the nature of the desired effect, the application rates are between 0.025 and 2, preferably from 0.1 to 1, kg of active compound per ha.

In the treatment of seed, amounts of active compound of generally from 0.001 to 50, preferably from 0.01 to 10, g per kilogram of seed are required.

In the use form as fungicides, the compositions according to the invention can also be present together with other active compounds, for example with herbicides, insecticides, growth regulators, fungicides or else with fertilizers.

When the compounds are mixed with fungicides, in many cases this results in a broadening of the fungicidal activity spectrum.

The following list of fungicides which can be applied jointly with the compounds according to the invention is meant to illustrate the possible combinations, without imposing a limitation: fungicides from the active compound group of the sulfur compounds, dithibcarbamates and their derivatives; nitro derivatives; heterocyclic substances, such as, for example, imidazoline derivatives, triazoles, triazine derivatives, quinoxaline derivatives, benzimidazole derivatives, thiadiazole derivatives, etc.; or strobilurins.

The following working examples illustrate the invention in more detail:

EXAMPLE 1

N-(3-chlorophenyl)-2-cyano-2-phenylacetamide (Compound No. 2 from Table 1) 3 g (0.016 mol) of ethyl phenylcyanoacetate and 2 g (0.016 mol) of 3-chloroaniline are heated undiluted at 130° C. for 5 hours. The mixture is subsequently taken up in 100 ml of dichloromethane and extracted three times with 10% strength hydrochloric acid. The organic phase is separated off, dried and concentrated. The resulting residue is taken up in 30 ml of dichloromethane, and 200 ml of petroleum ether are added. The resulting crystalline precipitate is filtered off with suction, washed with petroleum ether and dried. Yield 38%; m.p. 123° C.

EXAMPLE 2

Herbicidal Action

The herbicidal action of the compounds according to the invention is investigated using the representative test model below. The effect of the test substances on the growth of duck weed is determined by the following method:

The duct weed *Lemna paucicostata* was grown under sterile conditions and 250 ml glass vessels containing 100 ml of inorganic nutrient solution and supplemented with 1% sucrose, as described by Grossmann et al., Pesticide Science 35, (1992), 283–289. At the beginning of the test, 150 μl of a solution of active compound in acetone (stock solution: 100-fold concentrated) were pipetted into Petri dishes (diameter 6 cm, height 1.5 cm; Greiner, Frickenhausen) containing 15 ml of nutrient solution. (without added sucrose). Only the solvent component of the active compound solution was added to the nutrient solution for the control tests. Then, 4 Lemna plants were introduced into each dish, the dishes were covered with lids and incubated under permanent light conditions at 25° C. After 8–10 days, the increase in leaf area was determined using an imaging apparatus (Imago, Compulog Computer Syst., Böblingen) as growth parameter, and this was used to calculate the growth inhibition as a percentage relative to the control.

The results of the tests can be seen from the table which follows. The herbicidal effect of the compounds according to the invention is demonstrated by the potent inhibition of the growth of Lemna.

| Compound | Concentration (μmolar) | Growth inhibition (% relative to the control) |
|---|---|---|
| A | 100 | 100 |
|   | 10  | 93  |
|   | 1   | 40  |

A = N-(3, 4-dichlorophenyl)-2-cyano-2-phenylacetamide (Table 1, Comp. No. 8)

EXAMPLE 3
Fungicidal Action
Activity against *Pyricularia oryzae* (protective)

Leaves of potted rice seedlings c.v. "Tai-Nong 67" were sprayed to run off point with an aqueous preparation of active compound which had been prepared from a stock solution comprising 10% of active compound, 63% of cyclohexanone and 27% of emulsifier. The following day, the plants were inoculated with an aqueous spore suspension of *Pyricularia oryzae*. The test plants were subsequently placed in controlled-environment chambers at 22–24° C. and 95–99% relative atmospheric humidity for 6 days. The extent of the development of the infection on the leaves was then determined visually.

| Active compound from Table 1 | % infection of the leaves after application of an aqueous preparation containing 250 ppm of active compound |
|---|---|
| No. 5 | 15 |
| No. 7 | 7 |
| No. 14 | 15 |
| No. 15 | 5 |
| Control (untreated) | 85 |

EXAMPLE 4
Fungicidal Action
Activity Against *Plasmopara viticola*

Leaves of potted grapevines c.v. "Müller-Thurgau" were sprayed to run off point with an aqueous preparation of active compound which had been prepared using a stock solution comprising 10% of active compound, 63% of cyclohexanone and 27% of emulsifier. In order to be able to assess the persistency of the substances, the plants were kept for 7 days in a greenhouse after the spray coating had dried on. Only then were the leaves inoculated with an aqueous zoospore suspension of *Plasmopara viticola*. The grapevines were then initially kept in a water vapor-saturated chamber at 24° C. for 48 hours and then in a greenhouse at 20 and 30° C. for 5 days. After this period of time, the plants were once more kept in a humid chamber for 16 hours to promote sporangiophore eruption. The extent of the infection on the undersides of the leaves was then determined visually.

| Active compound from Table 1 | % infection of the leaves after application of an aqueous preparation containing 250 ppm of active compound |
|---|---|
| No. 2 | 0 |
| No. 14 | 0 |
| No. 18 | 10 |
| Control (untreated) | 90 |

We claim:
1. A method for controlling harmful fungi; or for controlling undesirable growth of harmful plants, which comprises bringing
   i) the fungi, their habitat or materials, plants, seeds, soils, areas or spaces to be protected against fungal attack, and/or
   ii) the harmful plants or their habitat into contact with an effective amount of at least one compound of the formula I

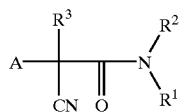

where the radicals have the following meanings:
A is aryl which can be mono- or polysubstituted by the following groups: hydrogen, halogen, cyano, nitro, hydroxyl, mercapto, thiocyanato, carboxyl, amino, $C_1$–$C_6$-alkyl, $C_1$–$C_6$-alkoxy-$C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_2$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkoxy, $C_1$–$C_6$-alkyl-$C_3$–$C_7$-cycloalkoxy, $C_3$–$C_7$-halocycloalkyl, $C_3$–$C_7$-cyanocycloalkyl, $C_3$–$C_7$-halocycloalkoxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyano-cycloalkenyl, $C_5$–$C_7$-halocycloalkenyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxyl-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulfinyl, arylsufonyl, heteroarylsulfinyl, heteroarylsulfonyl, aryl-$C_1$–$C_6$-alkyl, aryl-$C_2$–$C_6$-alkenyl, aryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, $C_1$–$C_6$-alkylsulphinyl, $C_1$–$C_6$-alkylsulphonyl, $C_1$–$C_6$-alkylamino, di-$C_1$–$C_6$-alkylamino, aryl, aryloxy, arylthio or —C($R^4$)=$NR^5$, $R^1$ is aryl or aryl-$C_1$–$C_6$-alkyl, where the aryl radical can in each case be mono- or polysubstituted by the following groups: hydrogen, halogen, cyano, nitro, hydroxyl, mercapto, thiocyanato, carboxyl, amino, $C_1$–$C_6$-alkyl, $C_1$–$C_6$-alkoxy-$C_1$–$C_6$-alkyl, $C_1$–$C_6$-cyanoalkyl, $C_2$–$C_6$-alkenyl, $C_1$–$C_6$-alkoxy-$C_2$–$C_6$alkenyl -$C_2$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkoxy, $C_1$–$C_6$-alkyl-$C_3$–$C_7$-cycloalkoxy, $C_3$–$C_7$-halocycloalkyl, $C_3$–$C_7$-cyanocycloalkyl, $C_3$–$C_7$-halocycloalkoxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxyl-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulphinyl, arylsulphonyl, heteroarylsulphinyl, heteroarylsulphonyl, aryl-$C_1$–$C_6$-alkyl, aryl-$C_2$–$C_6$-alkenyl, aryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, $C_1$–$C_6$-alkylsulphinyl, $C_1$–$C_6$-alkylsulphonyl, $C_1$–$C_6$-alkylamino, di-$C_1$–$C_6$-alkylamino, aryl, aryloxy, arylthio or —C($R^4$)=$NR^5$, $R^2$, $R^3$ are hydrogen, $C_1$–$C_6$-alky, $C_2$–$C_6$-alkenyl, $C_3$–$C_7$-cycloalkyl, $C_1$–$C_6$-alkylaryl, which may be unsubstituted or partially or fully halogenated or may carry one to three substituents selected from the group consisting of $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl;

$R^4$ is hydrogen or $C_1$–$C_6$-alkyl, $R^5$ is hydroxyl, $C_1$–$C_4$-alkoxy, aryl-$C_1$–$C_4$-alkoxy, aryloxy, or an agriculturally useful salt thereof or a composition comprising at least one of these compounds.

2. The method as claimed in claim 1, where A is not unsubstituted phenyl if $R^3$ is hydrogen or $C_1$–$C_5$-alkyl and $R^1$ is aryl, halogen-substituted aryl or arlyalkyl.

3. The method as claimed in claim 1, where A is unsubstituted or substituted phenyl or naphthyl.

4. The method as claimed in claim 1, where $R^1$ is unsubstituted or substituted phenyl.

5. The method as claimed in claim 1, where $R^2$ is hydrogen.

6. The method as claimed in claim 1, where $R^3$ is hydrogen; $C_1$–$C_6$-alkyl or $C_3$–$C_7$-cycloalkyl.

7. The method as claimed in claim 1, where A or $R^1$ is substituted phenyl, the phenyl ring being mono-, di- or trisubstituted by halogen, alkyl, alkoxy, nitro, cyano, haloalkyl or phenyl.

8. The method as claimed in claim 7, where the phenyl ring is monosubstituted by halogen, alkyl, alkoxy, nitro, haloalkyl or cyano.

9. The method as claimed in claim 8, where the phenyl ring has the following meanings: 4-halophenyl, 4-alkylphenyl, 4-alkoxyphenyl, 4-nitrophenyl, 4-cyanophenyl, 4-trifluoromethylphenyl, 2-halophenyl, 2-alkylphenyl, 2-alkoxyphenyl, 2-nitrophenyl, 2-cyanophenyl, 2-trifluoromethylphenyl, 3-halophenyl 3-alkylphenyl, 3-alkoxyphenyl, 3-nitrophenyl, 3-cyanophenyl, 3-trifluoromethylphenyl.

10. The method as claimed in claim 7, where the phenyl ring is disubstituted by halogen or alkyl.

11. The method as claimed in claim 10, where the phenyl ring has the following meanings: 2,3-dihalophenyl; 2,4-dihalophenyl; 2,5-dihalophenyl; 2,6-dihalophenyl; 3,4-dihalophenyl; 3,5-dihalo- phenyl; 2,3-dimethylphenyl; 2,4-dimethylphenyl; 2,5-dimethyl- phenyl; 2,6-dimethylphenyl; 3,4-dimethylphenyl or 3,5-dimethylphenyl.

12. A compound selected from:
N-(3-chlorphenyl)-2-cyano-2-phenylacetamide;
N-(2,5-dichlorphenyl)-2-cyano-2-phenylacetamide;
N-(2,6-dichlorphenyl)-2-cyano-2-phenylacetamide;
N-(3,5-dichlorphenyl)-2-cyano-2-phenylacetamide;
N-(3-chlorphenyl)-2-cyano-2-phenylpropamide;
N-(4-fluorphenyl)-2-cyano-2-phenylacetamide;
N-(2-fluorphenyl)-2-cyano-2-phenylacetamide;
N-(3-fluorphenyl)-2-cyano-2-phenylacetamide;
N-(4-fluorphenyl)-2-cyano-2-phenylpropamide;
N-(2-fluorphenyl)-2-cyano-2-phenylpropamide;
N-(3-fluorphenyl)-2-cyano-2-phenylpropamide.

13. The method of claim 6, wherein $R^3$ is hydrogen, methyl, ethyl, propyl or cyclopropyl.

14. A crop protection composition comprising at least one compound of formula I

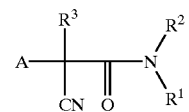

I wherein

A is aryl which can be mono- or polysubstituted by the following groups: hydrogen, halogen, cyano, mitre, hydroxyl, mercapto, thiocyanato, carboxyl, amino, $C_1$–$C_6$-alkyl, $C_1$–$C_6$-alkoxy-$C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_2$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkoxy, $C_1$–$C_6$-alkyl-$C_3$–$C_7$-cycloalkoxy, $C_3$–$C_7$-halocycloalkyl, $C_3$–$C_7$-cyanocycloalkyl, $C_3$–$C_7$-halocycloalkoxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkyl-carboxyl-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulfinyl, arylsufonyl, heteroarylsulfinyl, heteroarylsulfonyl, aryl-$C_1$–$C_6$-alkyl, aryl-$C_2$–$C_6$-alkenyl, aryl-$C_3$–$C_6$- alkynyl, aryl-$C_2$–$C_6$-alkoxy, aryl-$C_2$–$C_6$-alkenyloxy, aryl-$C_3$–$C_6$-alkynyloxy, $C_1$–$C_6$-alkylsulphinyl, $C_1$–$C_6$-alkylsulphonyl, $C_1$–$C_6$-alkylamino, di-$C_1$–$C_6$-alkylamino, aryl, aryloxy, arylthio or —$C(R^4)$=$NR^5$, $R^1$ is aryl or aryl-$C_1$–$C_6$-alkyl, where the aryl radical can in each case be mono- or polysubstituted by the following groups: hydrogen, halogen, cyano, nitro, hydroxyl, mercapto, thiocyanato, carboxyl, amino, $C_1$–$C_6$-alkyl, $C_1$–$C_6$-alkoxy-$C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_2$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkoxy, $C_1$–$C_6$-alkyl-$C_3$–$C_7$-cycloalkoxy, $C_3$–$C_7$-halocycloalkyl, $C_3$–$C_7$-cyanocycloalkyl, $C_3$–$C_7$-halocycloalkoxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_2$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxyl-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulphinyl, arylsulphonyl, heteroarylsulphinyl, heteroarylsulphonyl, aryl-$C_1$–$C_6$-alkyl, aryl-$C_2$–$C_6$-alkenyl, aryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, $C_1$–$C_6$-alkylsulphinyl, $C_1$–$C_6$-alkylsulphonyl, $C_1$–$C_6$-alkylamino, di-$C_1$–$C_6$-alkylamino, aryl, aryloxy, arylthio or —$C(R^4)$=$NR^5$, $R^2$, $R^3$ are hydrogen, $C_1$–$C_6$-alkyl, $C_2$–$C_6$-alkenyl, $C_3$–$C_7$-cycloalkyl, $C_1$–$C_6$-alkylaryl, which may be unsubstituted or partially or fully halogenated or may carry one to three substituents selected from the group consisting of $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl;

$R^4$ is hydrogen or $C_4$–$C_6$-alkyl, $R^5$ is hydroxyl, $C_1$–$C_4$-alkoxy, aryl-$C_1$–$C_4$-alkoxy, aryloxy, with the proviso that if A is an unsubstituted phenyl group and $R^3$ is hydrogen or alkyl, $R^1$ is not aryl, arylalkyl or halogen-substituted aryl, and the proviso that if $R^3$ is hydrogen, A is not 2-nitrophenyl or 2-aminophenyl.

15. A compound of formula I

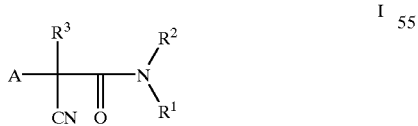

wherein

A is aryl which can be mono- or polysubstituted by the following groups: hydrogen, halogen, cyano, mitre, hydroxyl, mercapto, thiocyanato, carboxyl, $C_1$–$C_6$-alkyl, $C_1$–$C_6$-alkoxy-$C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_2$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkoxy, $C_1$–$C_6$-alkyl-$C_3$–$C_7$-cycloalkoxy, $C_3$–$C_7$-halocycloalkyl, $C_3$–$C_7$-cyanocycloalkyl, $C_3$–$C_7$-halocycloalkoxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxyl-$C_1$–$C_6$-alkyl, $C_1$–$C_6$-alkylcarbonyl-$C_1$–$C_6$-alkyl, $C_1$–$C_6$-alkylcarbonylamino, heteroarylsulfinyl, heteroarylsulphonyl, $C_1$–$C_6$-alkylsulphinyl, $C_1$–$C_6$-alkylsulphonyl, $C_1$–$C_6$-alkylamino, di-$C_1$–$C_6$-alkylamino, or —$C(R^4)$=$NR^5$, $R^1$ is aryl or aryl-$C_1$–$C_6$-alkyl, where the aryl radical can in each case be mono- or polysubstituted by the following groups: hydrogen, halogen, cyano, nitro, hydroxyl, mercapto, thiocyanato, carboxyl, amino, $C_1$–$C_6$-alkyl, $C_1$–$C_6$-alkoxy-$C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_2$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkoxy, $C_1$–$C_6$-alkyl-$C_3$–$C_7$-cycloalkoxy, $C_3$–$C_7$-halocycloalkyl, $C_3$–$C_7$-cyanocycloalkyl, $C_3$–$C_7$-halocycloalkoxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxyl-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulphinyl, arylsulphonyl, heteroarylsulphinyl, heteroarylsulphonyl, aryl-$C_1$–$C_6$-alkyl, aryl-$C_2$–$C_6$-alkenyl, aryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, $C_1$–$C_6$-alkylsulphinyl, $C_1$–$C_6$-alkylsulphonyl, $C_1$–$C_6$-alkylamino, di-$C_1$–$C_6$-alkylamino, aryl, aryloxy, arylthio or —$C(R^4)$=$NR^5$, $R^2$, $R^3$ are hydrogen, $C_1$–$C_6$-alkyl, $C_2$–$C_6$-alkenyl, $C_3$–$C_7$-cycloalkyl, $C_1$–$C_6$-alkylaryl, which may be unsubstituted or partially or fully halogenated or may carry one to three substituents selected from the group consisting of $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl;

$R^4$ is hydrogen or $C_4$–$C_6$-alkyl, $R^5$ is hydroxyl, $C_1$–$C_4$-alkoxy, or a salt thereof, except for the compounds wherein (a) A is unsubstituted phenyl, $R^3$ is hydrogen or alkyl, and $R^1$ is unsubstituted phenyl or halogen-substituted phenyl, (b) A is unsubstituted phenyl, $R^3$ is hydrogen or $C_1$–$C_5$-alkyl, and $R^1$ is aryl, halogen-substituted aryl or arylakyl, (c) $R^1$ is phenyl, naphtyl or phenyl-$C_1$–$C_4$-alkyl, $R^2$ is hydrogen, alkyl, alkenyl or $C_5$–$C_7$-cycloalkyl, and $R^3$ is hydrogen, and (d) A is 2-nitrophenyl or 2-aminophenyl and $R^3$ is hydrogen;

and except for the following compounds:

N-(4-ethoxyphenyl)-2-cyano-2-phenyl hexamide;
N-(4-ethoxyphenyl)-2-cyano-2-phenylbutamide;
N-(2,4,6-trimethoxyphenyl)-2-cyano-2-phenylacetamide;
N-(2,6-dimethylphenyl)-2-cyano-2-(4-methoxyphenyl) acetamide;
N-(2-methylphenyl)-2-cyano-2-phenylacetamide;
N-(3-methylphenyl)-2-cyano-2-phenylacetamide;
N-(4-methylphenyl)-2-cyano-2-phenylacetamide.

16. The compound defined in claim 15, wherein A is unsubstituted or substituted phenyl or naphthyl.

17. The compound defined in claim 15, wherein $R^1$ is unsubstituted or substituted phenyl.

18. The compound defined in claim 15, wherein $R^2$ is hydrogen.

19. The compound defined in claim 15, wherein $R^3$ is hydrogen, $C_1$–$C_6$-alkyl or $C_3$–$C_7$-cycloalkyl.

20. The compound defined in claim 15, wherein $R^3$ is hydrogen, methyl, ethyl, propyl or cyclopropyl.

21. The compound defined in claim 15, wherein if A is substituted phenyl, the phenyl ring is mono-, di- or trisubstituted by halogen, alkyl, alkoxy, cyano, haloalkyl or phenyl, and if $R^1$ is substituted phenyl, the phenyl ring is mono-, di- or trisubstituted by halogen, alkyl, alkoxy, nitro, cyano, haloakyl or phenyl.

22. The compound defined in claim 21, wherein the phenyl ring in position A is monosubstituted by ahlogen, alkyl, alkoxy, haloalkyl or cyano; and the phenyl ring in position $R^1$ is monosubstituted by halogen, alkyl, alkoxy, nitro, haloalkyl or cyano.

23. The compound defined as claim 22, wherein A has the following meanings: 4-halophenyl, 4-alkylphenyl, 4-alkoxyphenyl, 4-cyanophenyl, 4-trifluoromethylphenyl, 2-halophenyl, 2-alkylphenyl, 2-alkoxyphenyl, 2-cyanophenyl, 2-trifluoromethylphenyl, 3-halophenyl, 3-alkylphenyl, 3-alkoxyphenyl, 3-cyanophenyl or 3-trifluoromethylphenyl, and $R^1$ has the following meanings: 4-halophenyl, 4-alkylphenyl, 4-alkoxyphenyl, 4-nitrophenyl, 4-cyanophenyl, 4-trifluoromethylphenyl, 2-halophenyl, 2-alkylphenyl, 2-alkoxyphenyl, 2-nitrophenyl, 2-cyanophenyl, 2-trifluoromethylphenyl, 3-halophenyl, 3-alkylphenyl, 3-alkoxyphenyl, 3-nitrophenyl, 3-cyanophenyl or 3-trifluoromethylphenyl.

24. The compound defined in claim 21, wherein the phenyl ring in position A or $R^1$ is disubstituted by halogen or alkyl.

25. The compound defined in claim 24, wherein the phenyl ring in position A or $R^1$ has the following meanings: 2,3-dihalophenyl; 2,4-dihalophenyl; 2,5-dihalophenyl; 2,6-dihalophenyl; 3,4-dihalophenyl; 3,5-dihalophenyl; 2,3-dimethylphenyl; 2,4-dimethylphenyl; 2,5-dimethylphenyl; 2,6-dimethylphenyl; 3,4-dimethylphenyl or 3,5-dimethylphenyl.

* * * * *

UNITED STATES PATENT AND TRADEMARK OFFICE
CERTIFICATE OF CORRECTION

PATENT NO. : 6,613,931 B1
DATED : September 2, 2003
INVENTOR(S) : Wagner et al.

It is certified that error appears in the above-identified patent and that said Letters Patent is hereby corrected as shown below:

<u>Title page,</u>
Item [57], ABSTRACT,
Line 1, "resent" should be -- present --.

<u>Column 25,</u>
Line 10, "$C_2$-$C_6$-alkenyl - $C_2$-$C_6$-alkynyl," should be -- $C_2$-$C_6$-alkenyl, $C_2$-$C_6$-alkynyl --;
Line 50, "arlyalkyl" should be -- arylalkyl --.

<u>Column 26,</u>
Line 42, "mitre" should be -- nitro --.

<u>Column 27,</u>
Line 1, "aryl-$C_2$-$C_6$-alkoxy" should be -- aryl-$C_1$-$C_6$-alkoxy --;
Line 25, "$C_2$-$C_6$-alkylthio" should be -- $C_1$-$C_6$-alkylthio --;
Line 45, "$C_4$-$C_6$-alkyl" should be -- $C_1$-$C_6$-alkyl --;
Line 63, delete "mitre".

<u>Column 28,</u>
Line 61, "$C_4$-$C_6$-alkyl" should be -- $C_1$-$C_6$-alkyl --.

<u>Column 30,</u>
Line 4, "ahlogen" should be -- halogen --.

Signed and Sealed this

Twenty-third Day of March, 2004

JON W. DUDAS
*Acting Director of the United States Patent and Trademark Office*